United States Patent [19]

Cochrum et al.

[11] Patent Number: 5,578,314
[45] Date of Patent: Nov. 26, 1996

[54] MULTIPLE LAYER ALGINATE COATINGS OF BIOLOGICAL TISSUE FOR TRANSPLANTATION

[75] Inventors: Kent C. Cochrum, Davis; Randel E. Dorian, Orinda; Susan A. Jemtrud, San Francisco, all of Calif.

[73] Assignee: The Regents of the University of California, Oakland, Calif.

[21] Appl. No.: 186,327

[22] Filed: Jan. 24, 1994

Related U.S. Application Data

[63] Continuation-in-part of Ser. No. 891,564, filed as PCT/US93/05461, Jun. 1, 1993, Pat. No. 5,429,821.

[51] Int. Cl.$^6$ .................. A61F 2/02; A01N 1/02; C12N 5/08

[52] U.S. Cl. ............. 424/424; 424/423; 264/4.1; 435/1.1; 435/177; 435/178; 435/179; 435/180; 435/182; 435/240.22; 435/240.241; 435/240.243; 623/11

[58] Field of Search .................. 424/423, 424; 435/1, 182, 177, 178, 179, 180, 240.241, 240.243; 128/1 R; 264/4.1; 623/11

[56] References Cited

U.S. PATENT DOCUMENTS

| | | | |
|---|---|---|---|
| 4,352,883 | 10/1982 | Lim | 435/178 |
| 4,391,909 | 7/1983 | Lim | 435/178 |
| 4,663,286 | 5/1987 | Tsang et al. | 435/178 |
| 4,673,566 | 6/1987 | Goosen et al. | 424/19 |
| 4,689,293 | 8/1987 | Goosen et al. | 435/1 |
| 4,696,286 | 9/1987 | Cochrum | 128/1 |
| 4,744,933 | 5/1988 | Rha et al. | 264/4.3 |
| 4,749,620 | 6/1988 | Rha et al. | 428/402.2 |
| 4,789,550 | 12/1988 | Hommel et al. | 424/493 |
| 4,806,355 | 2/1989 | Goosen et al. | 424/424 |
| 5,175,093 | 12/1992 | Seifert | 435/41 |
| 5,227,298 | 7/1993 | Weber et al. | 435/178 |
| 5,334,640 | 8/1994 | Desai et al. | 524/56 |

FOREIGN PATENT DOCUMENTS

| | | |
|---|---|---|
| 2034641 | 1/1991 | Canada. |
| 2034633 | 1/1991 | Canada. |
| 9107951 | 6/1991 | WIPO. |
| 9324112 | 12/1993 | WIPO. |

OTHER PUBLICATIONS

Haug, Arne, *Fractionation of Alginic Acid*, Acta Chem. Scand. 13, No. 3, pp. 601–603, (1959).

Chang, Thomas, M. S., *Semipermeable Microcapsules*, Science, vol. 146, pp. 524–525, (1964).

Haug, Arne, et al., *Fractionation of Alginates by Precipitation with Calcium and Magnesium Ions*, Acta Chem. Scand., No. 5, pp. 1221–1226, (1965).

Mosbach, Klaus, *Entrapment of Enzymes and Microorganisms in Synthetic Cross–linked Polymers and their Application in Column Techniques*, Acta Chem. Scand., No. 10, pp. 2807–2810, (1966).

Chang, Thomas, M. S., et al., *Semipermeable Aqueous Microcapsules*, Canadian Journal of Physiology and Pharmacology, vol. 44, pp. 115–128, (1966).

(List continued on next page.)

Primary Examiner—Carlos Azpuru
Attorney, Agent, or Firm—Hana Verny

[57] ABSTRACT

A method for multiple layer coating of biological tissue and cells for transplantation. The cell or tissue transplants are coated with multiple coatings of purified alginate. The method includes applying the first coat of sodium alginate gelled with divalent cations followed by optional treatment with strontium, barium or other divalent cation, resuspending the single coated droplets in sodium alginate and forming the halo layer around the first coating via exchange or diffusion of divalent cations from the single coating to the surrounding soluble alginate, removing the excess coating and gelling the remaining thin layer of soluble alginate with divalent cations. The coated transplants have distinct structure where biological tissue or cell core is covered with the first alginate coat, which is surrounded by an intermediate halo layer which is covered by the outer coating.

25 Claims, 9 Drawing Sheets

OTHER PUBLICATIONS

Haug, Arne, et al., *Studies on the Sequence of Uronic Acid Residues in Alginic Acid*, Acta Chem. Scand. 21, No. 3, pp. 691–704, (1967).

Smidsrod, Olav, et al., *Dependence upon Uronic Acid Composition of Some Ion–Exchange Properties of Alginates*, Acta Chem. Scand. 22, No. 6, pp. 1989–1997, (1968).

Kierstan, M., et al., *The Immobilization of Microbial Cells, Subcellular Organelles, and Enzymes in Calcium Alginate Gels*, Biotechnology and Bioengineering, vol. XIX, pp. 387–397, (1977).

Klomp, G. F., et al., *Hydrogels for Encapsulation of Pancreatic Islet Cells*, Trans. Am. Soc. Artif. Intern. Organs, vol. XXV, pp. 74–76, (1979).

Plunkett, Marian, L., et al., *Methods in Laboratory Investigation*, Laboratory Investigation, vol. 62, No. 4, pp. 510–517, (1990).

Lim, Franklin, *Microencapsulated Islets as Bioartificial Endocrine Pancreas*, Science, vol. 210, pp. 908–910, (Nov. 1980).

Lim, Franklin, *Microencapsulation of Living Cells and Tissues*, Journal of Pharmaceutical Sciences, vol. 70, No. 4, pp. 351–354, (Apr. 1981).

Nilsson, Kjell, et al., *A General Method for the Immobilization of Cells with Preserved Viability*, European Journal of Applied Microbiology and Biotechnology, 17:319–326, (1983).

Gin, H., et al., *Agarose encapsulation of islets of Langerhans: reduced toxicity* in vitro, J. Microencapsulation, vol. 4, No. 3, pp. 239–242, (1987).

Nigam, Somesh, C., *Techniques for Preparing Hydrogel Membrane Capsules*, Biotechnology Techniques, vol. 2, No. 4, pp. 271–276, (1988).

Martinsen, A., *Alginate as Immobilization Material: I. Correlation between Chemical and Physical Properties of Alginate Gel Beads*, Biotechnology and Bioengineering, vol. 33, pp. 79–89, (1989).

Skjak–Braek, Gudmund, et al., *Alginate as Immobilization Material. II: Determination of Polyphenol Contaminants by Fluorescence Spectroscopy, and Evaluation of Methods for Their Removal*, Biotechnology and Bioengineering, vol. 33, pp. 90–94, (1989).

Darguy, S., et al., *Comparative Study of Microencapsulated Rat Islets Implanted in Different Diabetic Models in Mice*, Hormone. Met. Res. Suppl., 26:209–213, (1990).

Fritschy, Wilbert, M., *Effect of Alginate Microencapsulation on In Vitro Insulin Release from Rat Pancreatic Islets*, Diabetes, vol. 40, pp. 37–43, (Jan. 1991).

Otterlei, Marit, et al., *Induction of Cytokine Production from Human Monocyte Stimulated with Alginate*, Journal of Immunotherapy, 10:286–291, (1991).

Soon–Shiong, P., *An Immunologic Basis for the Fibrotic Reaction to Implanted Microcapsules*, Transplantation Proceedings, vol. 23, No. 1, pp. 758–759, (Feb. 1991).

Lum, Zhao–Ping, et al., *Prolonged Reversal of Diabetic State in NOD Mice by Xenografts of Microencapsulated Rat Islets*, Diabetes, vol. 4, pp. 1551–1516, (Nov. 1991).

Goosen, Mattheus, F. A., et al., *Fundamentals of Animal Cell Encapsulation and Immobilization*, CRC Press, (1993).

Fujihara, Michio, et al., *An influence of the structure of alginate on the chemotactic activity of macrophages and the antitumor activity*, Carbohydrate Research, 243, pp. 211–216, (1993).

Haug, Arne, *Composition and Properties of Alginates*, Norwegian Institute of Seaweed Research, Report No. 30, (1964).

Smidsrod, Olav, *Some Physical Properties of Alginates in Solution and in the Gel State*, Norwegian Institue of Seaweed Research, Report No. 34, (1973).

FIG. 1A

| STEPS | PROCESS | SUSPENDING MEDIUM | APPEARANCE | MECHANISM |
|---|---|---|---|---|
| 1. Suspend | Suspending isolated cells in Na-alginate (alginate 1, high guluronate, high molecular weight) | Na-alg-1 sodium Alginate | | Na-alginate is soluble |
| 2. Form droplets | Using electrostatic generator air knife, spinning disk or other device for dispersing suspension in air | Air | | Mechanical generation of droplets (e.g., by spinning disc, electrostatic drop generator, air knife, ect.) |
| 3. Gel alginate (1st alginate coat) Gel | Collecting droplets in $Ca^{++}$ or other divalent cation | Divalent Cations e.g., Calcium Chloride | | $Ca^{++}$ interacts particularly with guluronate blocks to provide cooperative intermolecular binding, forming a gel. |
| 4. Exchange $Ca^{++}$ | Soaking gel capsules in $Ba^{++}$ or $Sr^{++}$ other cations or 2nd mixtures thereof | Divalent Cations e.g., Barium or Strontium Chloride | | $Ba^{++}$ or $Sr^{++}$ exchange for $Ca^{++}$ to bind weakly to mixed block and mannuronate blocks. |
| 5. Wash out excess soluble metal ion | Using iso-osmolar sucrose solution or other non-ionic, iso-osmolar solution | Iso-osmotic millieu e.g., Sucrose solution | | With no competing soluble ions present, weakly-bound $Ba^{++}$ or $Sr^{++}$ remain bound to alginate. Alternatively, a reduced concentration of soluble calcium is left the initial coating. |

FIG. 1B

| STEPS | PROCESS | SUSPENDING MEDIUM | APPEARANCE | MECHANISM |
| --- | --- | --- | --- | --- |
| 6. Form halo layer | Soaking coated cells in second alginate (alginate 2, high mannuronate medium mol. weight) and mixing | Na-alg-2 sodium Alginate | | Na from soluble alginate 2 exchanges with $Ba^{++}$ or $Sr^{++}$ weakly bound to mixed block and mannuronate blocks of alginate 1; alginate 2 is gelled by interaction of guluronate blocks of alginate 2 with $Ba^{++}$ or $Sr^{++}$ as it diffuses outward from capsule (1st alginate coating). Alternatively, residual soluble calcium diffuses outward from capsule and gels surrounding soluble alginate. |
| 7. Coat (Final outer coating) | Dispersing halo covered capsules in air using air knife or other droplet generating device | Air | | Mechanical generation of droplets, dispersing halo-covered, coated cells in air; a film of soluble Na-alginate remains outside of the halo coat. |
| 8. Collect in $Ca^{++}$ | Halo covered spheres gel in collecting calcium chloride solution to form final, outer gel coat | Divalent Cation e.g., Calcium Chloride | | Contacting $Ca^{++}$ causes outer film of alginates to gel forming "outer" alginate gel coat. |

FIG. 1C

| STEPS | PROCESS | SUSPENDING MEDIUM | APPEARANCE | MECHANISM |
|---|---|---|---|---|
| Core | ○ | | | |
| Na-alginate 1 | ○ | Sr/BrCl | ○ | Soluble Na-alginate |
| $CaCl_2$ | ○ | Na-alginate 2 | ○ | Gelled Alginate Film |

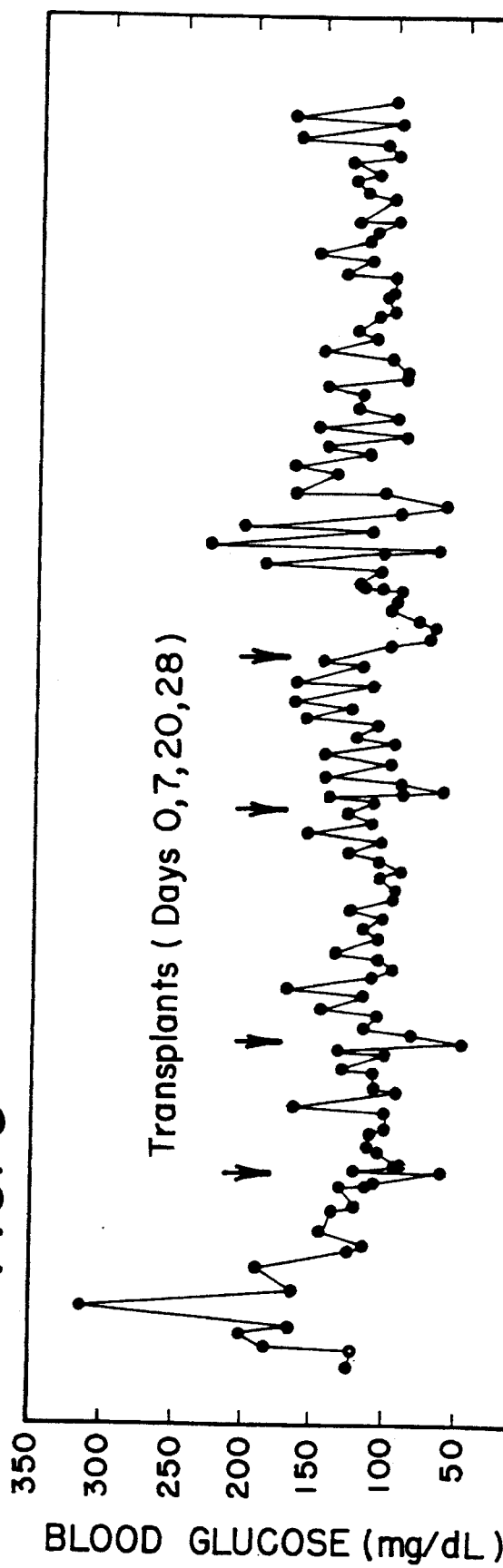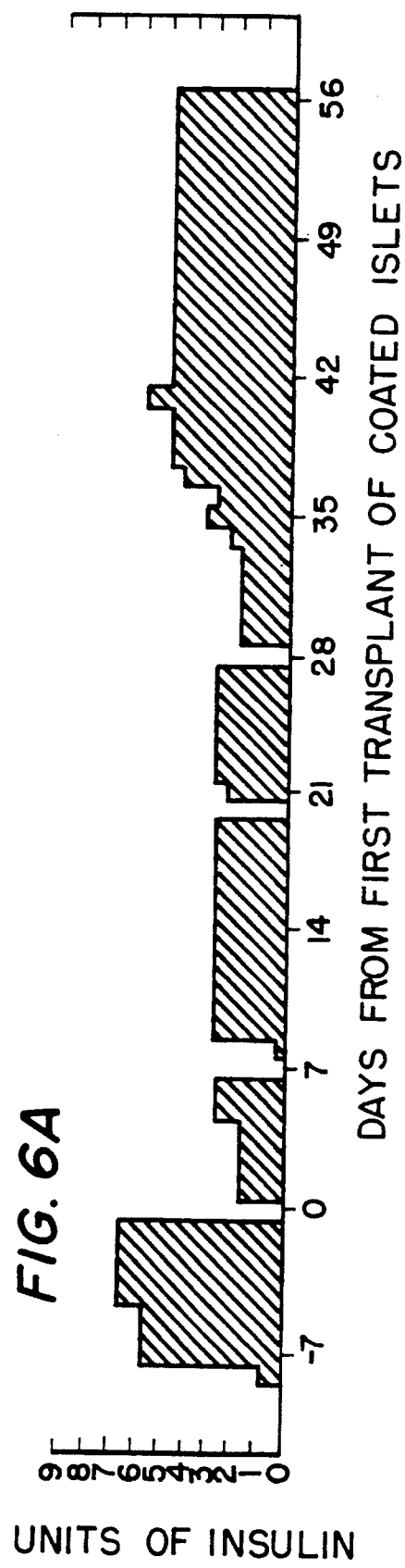
FIG. 6
FIG. 6A

DAYS FROM FIRST TRANSPLANT OF COATED ISLETS

MULTIPLE LAYER ALGINATE COATINGS OF BIOLOGICAL TISSUE FOR TRANSPLANTATION

This application is a continuation-in-part of application Ser. No. 07/891,564 filed May 29, 1992, now U.S. Pat. No. 5,429,821, PCT/US93/05461 filed on Jun. 1, 1993 and concurrently filed application entitled "Microcapsule Generating System and Method of Using Same", filed on Jan. 24, 1994, Ser. No. 08/185,709. All prior or concurrently filed applications are hereby incorporated by reference.

BACKGROUND OF THE INVENTION

Field of Invention

The current invention concerns a method for multiple layer alginate coating of biological tissue, cells and cell lines. In particular, the invention concerns cells or tissue coated with multiple layers of purified alginate. The method includes applying a first coat of soluble alginate gelled with divalent cations, optionally followed by treatment with other divalent cations, removing excess cations, resuspending the single coated cells or tissue in soluble alginate to form an intermediate halo layer around the first coating via exchange or diffusion of divalent cations from the single coating to the surrounding soluble alginate, dispersing the excess soluble alginate, and gelling the remaining thin layer of soluble alginate by contact with divalent cations to form an outer layer coating. Thus, a multi-layer structure is formed wherein biological tissue or cell core is covered with a first coat layer, which is optionally surrounded by an intermediate halo layer, which is in turn covered by an outer coating layer.

BACKGROUND AND RELATED DISCLOSURES

Traditional medical treatments for functional deficiencies of secretory and other biological organs have focused on replacing identified normal products of the deficient organ with natural or synthetic pharmaceutical agents or with cell or organ transplants. For example, for treating insulin-dependent diabetes mellitus where the pancreatic islets of Langerhans are nonfunctional, the normal secretion of insulin by the islets in the pancreas can be replaced either by daily administration of synthetic or substitute animal insulin, or by transplantation of functional human or animal islets.

Attempts to transplant organ tissues into genetically dissimilar hosts without immunosuppression are generally defeated by the immune system of the host. Attempts to provide effective protective barrier coatings to isolate the transplant tissues from the host immune system have not generally proven to be medically practical because the coating materials were incompatible with the host system or were otherwise unsuitable. The encapsulation or coating processes developed previously have not yielded reproducible coatings having the desired porosity and thickness required for the transplanted tissue to have a long and effective functional life in the host.

A successful cell or tissue transplant must be coated with a coating which will prevent its destruction by a host's immune system, which will prevent fibrosis, and which will be permeable to and allow a free diffusion of nutrients to the coated transplant and removal of the secretory and waste products from the coated transplant.

A primary problem with these coated cell or tissue transplants is that they are treated as foreign objects in the host's body and subject to immune rejection or destruction.

To protect transplants from destruction by the immune response of the host animal, various attempts have been made to create a protective barrier between the transplant tissue or cells and the immunological components of the host's system. *Science*, 146:524–525 (1964) described the microencapsulation of erythrocyte hemolysate and urease in semi-permeable polyamide membranes. However, these microcapsules did not survive for long when injected into the blood stream. Both the preparation of semi-permeable microencapsulated microbial cells and viable red blood cells, and also the possibility of using injections of encapsulated cells for organ replacement therapy were described in *Acta Chem. Scand.*, 20:2807–2812 (1966) and in *Can. J. Physiol. and Pharmacol.*, 44:115–128 (1966).

Multiple attempts have been made to use alginates for coating of cells and tissues. Compositions of alginates and methods for purifying and fractioning alginates have been generally described in *Composition and Properties of Alginates: Report No. 30*, Norsk Institute for Tang-og Tareforskning (Norwegian Institute of Seaweed Research) (1964); *Acta Chem. Scand.*, 13:601–603 (1959); *Acta Chem. Scand.*, 19:1221–1226 (1965); *Acta Chem. Scand.*, 21:691–704 (1967); *Acta Chem. Scand.*, 22:1989–1997 (1968); and *Biotech. and Bioeng.*, 33:90–94 (1989). Correlations between the chemical and physical properties of alginate gel beads have been reported in *Biotech. and Eng.*, 33:70–89 (1989).

Viable tissue and cells have been immobilized in alginate capsules coated with polylysine (*J. Pharm. Sci.*, 70:351–354 (1981). An attempt to use these coated capsules in pancreatic islet transplantation to correct the diabetic state of diabetic animals was reported in *Science*, 210:908–909 (1981). The methods described in the above reference, however, have not been able to achieve long term correction of diabetes in animals, and therefore have not been suitable for transplanting tissues, such as pancreatic islets, in humans.

*Diabetes*, 40:1511–1516 (1993) reported the prolonged reversal of the diabetic state of mice with xenografts of microencapsulated rat islets, using alginate-polylysine capsules. Substantial additional efforts are described in U.S. Pat. Nos. 4,673,566, 4,689,293, 4,789,550, 4,806,355, and 4,789,550, for example, to develop transplants encapsulated in calcium alginate capsules reacted with polylysine.

U.S. Pat. No. 4,744,933 describes encapsulating solutions containing biologically active materials in a membrane of inter-reacted alginate and polyamino acid.

U.S. Pat. No. 4,696,286 describes a method for coating transplants suitable for transplantation into genetically dissimilar individuals. The method involves coating the transplant with a surface-conforming bonding bridge of a multi-functional material that binds chemically to a surface component of the transplant, which is enveloped in a semi-permeable, biologically compatible layer of a polymer that binds chemically to the bonding bridge layer. A disadvantage of this method is that it relies upon specific interaction of the first polymer coating with acidic residues of proteins on the cell surface and thus may not provide complete coverage of tissues, particularly if other tissues are adhering to the tissue particles (e.g., acinar tissue on islets) and interfering with the desired bonding.

The use of calcium alginates for immobilization of microbial cells and enzymes is described in *J. Appl. Microbiol.*, 1:291–296 (1975) and *Biotech. and Bioeng.*, 19:387–397

(1977). Additionally, *Biotech. Tech.,* 2:271–276 (1988) describes methods for coating living cells in an outer membrane of calcium alginate by dropping a cell-containing calcium solution into an alginate solution and further incubating the capsules in a calcium solution.

*Lab. Invest.,* 90:6204–6205 (1990) describes an angiogenesis model using tumor cells entrapped in alginate beads where a spray of sodium alginate-cell suspension was contacted with aqueous calcium chloride solution to form calcium alginate beads.

Although alginates have been applied to coating food and pharmaceutical products, the use of alginates for coating living cells to produce a non-immunogenic coating which allows for long-term viability and function of the transplanted cells in a host animal has heretofore not been successful. Those working in this field have recognized that it is necessary to purify alginates for cell coating applications. For example, filtration has been suggested as a means to remove fibrotic fucan- and polyphenol-rich and other particulate contaminants. However, even such purified alginates themselves have been considered to be immunogenic. *Trans. Proc.,* 23:758–9, (1991) describes fibrous overgrowth of implanted alginate microcapsules in large animals. The study found that commercial alginates are often contaminated with polyphenols and other immunogenic materials and, even when purified by the methods employed, the commercial alginates having high mannuronic acid content were found to remain immunogenic and capable of activating macrophages in vivo resulting in production of fibrotic overgrowth. *Cell Trans.,* 1:165 (1992) corroborates the above findings and suggests that all alginates are inherently fibrogenic even when purified by methods employed in these studies. Others have suggested that a reason why the alginates are not biocompatible is that high mannuronate alginates stimulate human monocytes to produce cytokines and enhance macrophage migration cytokines (*J. Immunother.,* 10:286–291 (1991), and *Carbohydrate Research,* 243:211–216 (1993)).

Despite recognition in this field that purified alginates might be used for coating cells, long term non-immunogenic coated cell or tissue transplants have not been achieved at present.

One problem connected with previously reported alginate coatings is that they are either too thin, too thick or their thickness is not uniform. It is important that the coatings have a uniform thickness of within 20–200 μm. Alginate coatings having a thickness of greater than 200 μm have been reported to lack the permeability required for permitting the diffusion of nutrients and cell products through the coating in amounts sufficient for long term viability of the coated transplant while implanted in the host system. (*Horm. Met. Res. Suppl.,* 26:209–213 (1990).

Therefore a need continues to exist to provide transplant coatings which have a thickness within the acceptable limits of about 20–200 μm so that these transplants are not rejected by the host immune system and permit long-term viability and functionality of the transplanted cell or tissue.

U.S. Pat. No. 5,227,298 describes a method for introducing a second alginate gel coating to cells already coated with polylysine alginate. Both the first and second coating of this method require stabilization by polylysine.

Recently, purified alginate coatings have been successfully used to coat isolated pancreatic cells. Purification of these alginates was employed to remove phenolic and sulfate containing impurities and contaminants, which may be responsible for fibrogenicity of the nonpurified alginate.

This new process for purification of alginates, purified alginate and their use for coating of pancreatic and hepatic cells, and other biological tissue is described in copending patent applications Ser. No. 07/891,564, filed on May 29, 1992, now U.S. Pat. No. 5,429,821 herein by reference.

It would therefore be highly desirable to provide a method for a multiple coating of individual transplants which can withstand mechanical, chemical or immune destruction within the host, which would not provoke fibrogenic reactions impairing the transplant's function and which would additionally provide a uniform and controllable thickness of the coating to allow for free permeability of nutrients and secretory and waste products.

It is a primary object of the current invention to provide a method for a multiple layer coating suitable for coating of living and functional cells or tissues which provide a uniform coating having a thickness of between about 20–200 μm and which would eliminate fibrogenic and/or immune reactions destructive to the transplant's functionality and provides substantially complete coverage of the biological tissue core, thus allowing a successful long-term transplantation of these cells or tissues.

The present method differs substantially from all above cited references in that stabilization of the first and subsequent coat by polylysine or other polyamino acid or polycation is not required. The present method allows optionally the formation of a halo layer, providing an intermediate layer between an inner and outer coating that uniformly covers an exposed area of biological tissue.

All references and patents listed in this application are incorporated herein by reference in their entirety.

SUMMARY

One aspect of the current invention is a method for production of functional cell and tissue transplants coated with multiple layer coatings of purified alginate gel with uniform minimum thickness.

Another aspect of the current invention is a method for multiple coating of biological tissue or cell transplants wherein there are at least two gelled alginate coatings interspaced with a halo layer formed by an exchange of sodium or other non-gelling ions from soluble alginate for divalent cations, such as calcium, strontium or barium or other gelling ions from initial alginate gel coating.

Still another aspect of the current invention is an eight step method wherein a first alginate coat is applied to a suspension of cores of biological tissue or cells by (1) suspending the cores in an initial soluble alginate solution typically having a high content of guluronate; (2) mechanically forming droplets containing the suspended cores in a soluble alginate using electrostatic drop generator, air knife, spinning disc or other droplet forming device; (3) gelling the alginate with divalent cation, to produce gelled capsules; (4) optionally exchanging one divalent cation with another divalent cation, such as calcium, strontium or barium, by dispersing gelled capsules in a solution of divalent cation salts; (5) removing excess soluble divalent cation by washing the gelled capsules in iso-osmotic sucrose or other iso-osmotic non-ionic solution; (6) suspending gelled capsules in a second alginate and optionally forming a halo layer; (7) mechanically dispersing these capsules in air to remove excess soluble alginate; and (8) gelling these dispersed coated capsules in a divalent cation, to form an outer coating.

Still another aspect of the current invention is a method for production of multiple coated cell transplants having a laminated structure of a cell core coated by a first alginate coat surrounded by an intermediate halo layer covered with a final alginate coat wherein the coatings effectively provide a uniform covering for prolonged protection of the transplanted tissue cells from destruction by the host immune system.

Still another aspect of the current invention is a viable, functional and physiologically active multiple coated tissue or cell transplants that is physiologically acceptable to the host and provides a substitute for a dysfunctional organ or tissue and a therapy for such dysfunction.

Yet another aspect of the current invention relates to tissue or cells enclosed in a multi-layer coating having a thickness and a permeability allowing the effective diffusion and release into the host's system of products secreted by the multiple coated transplanted cells or tissue.

Yet another aspect of the current invention relates to tissue or cells enclosed in a multi-layer coating having a thickness permitting the diffusion to the transplanted cells or tissue of the amounts of nutrients and other substances required for their extended life and effective function after transplantation.

Still another aspect of the current invention relates to an effective transplantation of coated tissue material which is physiologically acceptable, non-fibrogenic and non-toxic to the host, and which can be used to provide a coating having the characteristics described above.

Still another aspect of the current invention is a process for effectively coating tissues and cell transplants with a substantially complete coating barrier which is physiologically acceptable, non-fibrogenic and non-toxic to the host and which provides a coating with a controlled thickness and permeability to intermediate size proteins.

Still another aspect of the current invention is the method for treatment of diabetes mellitus by administering to a patient pancreatic islets and cells coated with a multi-layer coating according to the invention.

Still another aspect of the current invention is the method for treatment of dysfunctions of liver, kidney, nerve cells, adrenal glands, thyroid gland, ovaries and other secretory organs by administering to a patient isolated healthy cells, tissues, cell lines, allografts or xenografts which are coated with a multiple layer coating according to the invention.

Still another aspect of the current invention is a treatment of pathological deficiencies by administering to a patient isolated cells coated with a multiple-layer coating according to the invention that can supply the substance(s) of interest.

BRIEF DESCRIPTION OF DRAWINGS

FIG. 1 illustrates a process for production of cell transplants with multiple layer alginate coating.

FIG. 6 depicts survival, blood glucose and insulin requirements in a pancreatectomized dog transplanted with single coated dog islets having approximately 10–30% exposed islet tissue.

DEFINITIONS

Figure 2:
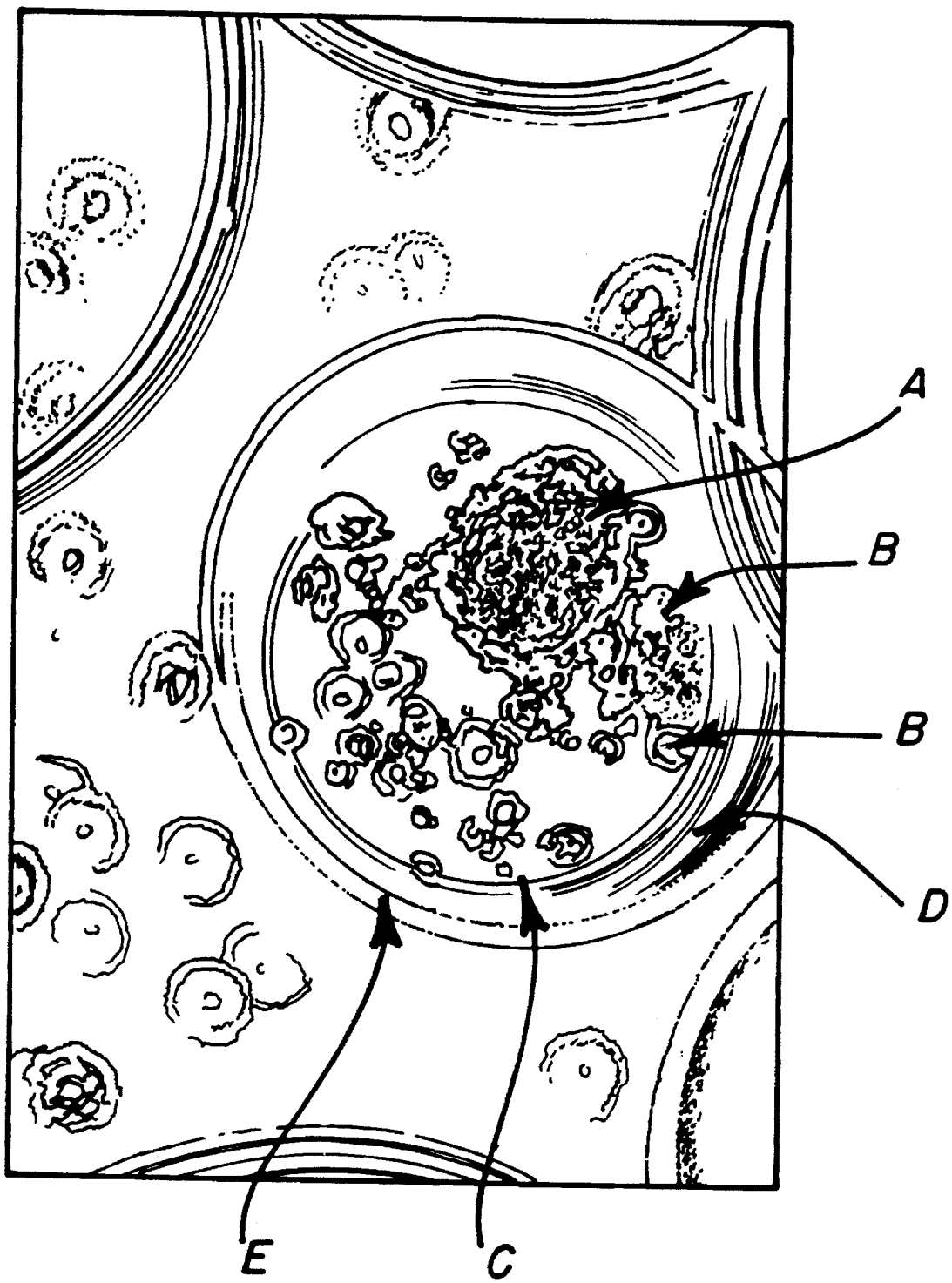
FIG. 2 is a drawing showing an isolated pancreatic islet coated with first and second alginate layers having an intermediate halo layer.

As used herein:

"Core" means living cells, biological tissue, cell lines or biological active substances, which are submitted to the present method for their encapsulation. Examples of such living cells, cell lines, and tissues are pancreatic islets, hepatic cells, neural cells, renal cortex cells, vascular endothelial cells, thyroid and parathyroid cells, adrenal cells, thymic cells, ovarian cells, allografts or xenografts. However, other types of cells or cell lines or biologically active substances intended to be implanted into the body of a host animal may also be utilized. These tissues or cells include, without limitation, tissue or cells removed from a donor animal, tissue or cells obtained by incubation or cultivation of donor tissues and cells, cells obtained from viable cell lines, biologically active products of cells or tissues, and the like.

"Transplant" means and includes a "core" as defined above, coated according to the invention. Any type of core for which transplantation is desired can be coated and transplanted according to this invention. Important tissues for transplants are secretory organ tissues, where transplantation from a donor organ to a host animal is desired to at least partially replicate the donor organ's action in the host system.

"Non-fibrogenic" means a composition which, when used to produce an implant having a diameter of 200 microns or less, does not induce bioisolation and resulting tissue death of the transplant by the immune system of a host through the process of fibrosis and macrophage overgrowth. In the case of transplantation of encapsulated islets, bioisolation and tissue death may be determined by monitoring insulin production from a pancreatic islet tissue transplant or by monitoring the maintenance of euglycemia in a diabetic host. The non-fibrogenic alginate of the invention is suitable for coating tissues or single cells using the coating technology according to this invention.

"Functional transplant" means the above transplant which is viable and functional in its normal way, that is, which produces or secretes products or hormones which it would normally produce endogenously in the donor body.

"Uniform thickness" means the thickness of the coating being between about 20 and about 200 μm wherein the thickness of the coating is preferably not below 20 μm and preferably not above 200 μm.

"Capsule or sphere" means single or double coated core which becomes a transplant according to the invention.

"Isotonic saline" means, unless specifically defined otherwise, 0.9% sodium chloride with 10 mM HEPES buffer.

"Calcium chloride solution or calcium solution" means, unless specifically defined otherwise, 1.7% calcium chloride dihydrate with 10 mM HEPES buffer.

"Sucrose water" means, unless specifically defined otherwise, 9.25% sucrose in water with 10 mM HEPES buffer.

"High guluronate" or "guluronate-rich" means the alginate containing a high ratio (>50%) of guluronate relative to mannuronate and typically having high molecular weight from about 80 to about 300 kilodaltons.

"High mannuronate" or "mannuronate-rich" means the alginate containing a high ratio (>50%) of mannuronate relative to guluronate and typically having medium molecular weight from about 40 to about 120 kilodaltons.

"Halo" means the halo layer placed between inner and outer gelled alginate layers and formed by exchange of divalent cations, such as calcium, strontium or barium, which may be bound to an initial coating with non-gelling counter ions of a soluble suspending alginate in a non-ionic medium or by diffusion of soluble gelling cations from the initial coating. The exchange or diffusion of cations gives rise to a gel halo layer extending from the initial coating into the suspending alginate to form a substantially complete alginate halo coating layer around the initial coating.

DETAILED DESCRIPTION OF THE INVENTION

The current invention is directed to the field of medical transplants of cells and tissues. Particularly, the invention concerns medical transplants containing viable and physiologically active cells and biological tissue, a "core" covered with multiple layers of alginate coating. The invention further concerns the process for the manufacture of such transplants and their use.

The transplants are coated with at least two layers of alginate. The inner and outer layers are optionally interspaced with a distinct halo layer. The halo is formed by exchange of divalent ions present in the gelled alginates, with non-gelling counter ions of the soluble alginate. In alternative, the halo can be formed by diffusion of soluble gelling cations from the initial coating. The invention offers several advantages over previously known and available methods for transplant coating.

First, transplants are coated with a uniform coating of at least two layers. This coating allows the cells or biological tissue to function normally. The coating's permeability allows the cell or tissue core product to diffuse to the host system and, at the same time, allows diffusion of nutrients to the core and removal of the core waste product from the core. The coatings have a long functional life and upon their destruction, if any, they do not cause toxic or other undesirable reactions because the coating is made of biologically acceptable materials. The multi-layer coating has a uniform thickness of between about 20 and about 200 μm which assures the normal functioning of the core and prevents the transplant from being destroyed by the immune reaction. The coating layers also utilize purified alginates which do not provoke host immune reactions.

Another advantage of the current invention is that the novel multi-layer coating of the transplant has a uniform thickness which can be applied to numerous cell or tissue cores in an efficient, convenient and reproducible manner. Optional formation of a halo layer prevents exposure of the biological tissue core and isolates the biological tissue from the host immune system. However, multi-layer coating without formation of the halo layer is also within the scope of this invention.

The multi-layer coating procedure is efficient for the mass production of transplants having alginate coatings with a thickness of less than about 200 μm. The transplants coated according to the invention function normally and for an extended period of time.

Another advantage of this invention is a substantial decrease of fibrotic and other detrimental reactions.

The method of this invention provides coated transplants which are substantially resistant to fibrosis, host immune rejections and other detrimental reactions upon implantation into a host. Transplants of cells coated with multiple layers of purified alginate substantially fail to produce fibrosis and when administered to diabetic animals are able to correct an insulin deficiency for an extended period of time.

Additionally, the current invention avoids the use of polylysine and other compounds commonly used for purpose of cell encapsulation.

Introducing a multi-layer coating interspaced with a halo layer obviates reactions such as the dissolution of calcium alginate gel by chelation of calcium. Such reactions may result in the presence of residual soluble alginate within the capsule which may leak from the capsule and cause a fibrotic reaction.

The present invention produces fully operable and functional transplants covered with substantially uniform coatings which do not require a secondary protection of the outer coating with polylysine. One embodiment includes an intermediate halo layer between two coatings. Such intermediate layer provides substantially uniform thickness of coating around the cell or tissue, thus ensuring a substantially complete coverage of all cells or tissue by a defined minimum thickness. The thickness and permeability of the coating of the current invention may be controlled by appropriate selection of alginates and conditions for exchange reactions or diffusion processes by which the halo is generated, as well as other factors.

I. MULTI-LAYER COATING METHOD

Briefly, the current invention concerns multiple layer coated transplants and a method for applying multiple, uniform alginate coatings to cells, biological tissue or other particles. The method is novel in that it permits coating the cell or tissue core with two layers of gelled alginate optionally interspaced with a halo layer. The alginate used for the first inner coating typically contains a high ratio of guluronate relative to mannuronate and is typically of higher molecular weight. However, any other suitable alginate may be advantageously used as the first alginate. The alginate used for the outer coating typically contains a high ratio of mannuronate to guluronate and is typically of lower molecular weight. Similarly, this alginate may be substituted with another suitable alginate. In this manner, the first alginate can be used for formation of the outer coating and the second alginate can be used for formation of the first layer or any suitable combination of other alginates can be used. The use of all alginates, whether commercially available or specifically prepared, whether purified or not is within the scope of this invention as long as these alginates are suitable in the process of this invention to produce multilayer coatings of core material.

Cation exchange reactions and extrusion of halo layer containing coated cells or tissue cores through any suitable droplet forming device, such as, for example an air knife, electrostatic droplet generator or spinning disc, and the capture of the formed droplets in polymerizing divalent cation solution, such as for example calcium, strontium or barium or other suitable divalent cations, results in formation of stabilized three-layer coatings. The three coatings are a first initial coating, a second halo intermediate layer coating, and a third outer coating. No other method utilizes such an exchange or diffusion reaction or produces such substantially complete coating. At the same time, the present method allows the preparation of coated transplants with acceptably small overall dimensions.

In practice, the core material is suspended in a soluble alginate typically in guluronate-rich alginate having high molecular weight, and dispersed by an air-knife, spinning disc droplet generator, electrostatic droplet generator or other droplet generating device. The dispersed droplets containing the core are captured in a gelling solution of crosslinking divalent cations, such as, for example $Ca^{++}$, $Sr^{++}$, $Ba^{++}$. Each crosslinking cation can be exchanged with a different cation, for example $Ba^{++}$ can be exchanged for $Ca^{++}$, or a combination of cations, for example a mixture of $Sr^{++}$ and $Ba^{++}$ can be exchanged for $Ca^{++}$. This exchange occurs primarily between the second divalent cation and the first divalent cation bound to mannuronate blocks and/or heterogenous blocks of the gelled alginate polymer. Soluble ions are washed out of the sample by any suitable iso-osmotic solution, such as for example, iso-osmolar sucrose water. The coated cells or particles are then resuspended in a soluble alginate, typically in mannuronate-rich alginate having medium molecular weight, dissolved in a non-ionic medium. Divalent cations bound to the primary coating exchange with the non-gelling counter ions of the soluble suspending alginate. Alternatively, soluble gelling cation remaining with or added to the coated cells or tissue is allowed to diffuse into the soluble suspending alginate. A halo layer of gelled alginate is formed around each coated cell or particle by interaction of the liberated gelling cations with the suspending alginate around the perimeter of the initial coating. After formation of the halo layer, the excess soluble alginate is removed by a suitable droplet generating device. The resulting droplets are captured in a crosslinking divalent cation solution, to gel the film of alginate and to form an outer coating around the initial coating and the halo layer.

In a preferred embodiment, the alginate solution is a sodium or potassium alginate solution, and the gelling solution contains a concentration of divalent ions sufficient to gel the alginate. The alginate solutions contain alginates preferably having mannuronate to guluronate moiety ratios of from 1:6 to 6:1, and preferably free from impurities which would impair the viability and longevity of tissue transplants.

Any type of tissue, cells or cell lines for which transplantation is desired can be coated and transplanted according to this invention. Important tissues for transplants are secretory organ tissues, where transplantation from a donor organ to a host animal is desired to at least partially replicate the donor organ's action in the host system. Preferred donor tissues are pancreatic islets, hepatic cells, neural cells, renal cortex cells, vascular endothelial cells, thyroid cells, adrenal cells, thymic cells and ovarian cells and cell lines. For secretory tissues such as pancreatic islets, the thickness of protective coatings is uniform and in the range of from about 20 to about 200 μm. The coatings also have the permeability required to permit effective diffusion of nutrients and other essential biological materials to the transplanted tissues and passage of transplant's products into the host system. The coatings are non-fibrogenic and protect the core of the transplant from immunologically effective concentrations of agents of the host immune system.

II. ALGINATES

Alginate is a linear polymer of mannuronic and guluronic acid residues. These residues are arranged in blocks of several adjacent guluronic acid residues, forming so called guluronate blocks, and blocks of adjacent mannuronic acid residues, forming so called mannuronate blocks. The mannuronic and guluronic blocks are interspersed with blocks of alternating guluronic and mannuronic acid residues forming heterogeneous or mixed blocks.

Monovalent cation alginate salts, such as sodium or potassium alginate, are soluble. Most divalent cations, such as calcium, strontium or barium interact with alginate to form gels. Because of the higher affinity of these divalent cations for guluronate compared with mannuronate blocks and because of steric considerations, cooperative binding of gelling divalent cations to guluronate within guluronate blocks provides the primary intermolecular crosslinking responsible for formation of stable alginate gels. Mannuronate and mixed blocks are not crosslinked due to their weaker affinity for the crosslinking divalent cation, but function as flexible interconnecting segments between interacted guluronate blocks. The resulting gel structure has the appearance of an egg box, as it is frequently called.

Different divalent cations have different affinities for mannuronate and guluronate and thus are differentially susceptible to exchange by other monovalent or divalent cations. Likewise, depending on the molecular weight, the number of residues per block and the overall ratio of guluronate to mixed or mannuronate blocks, different alginates have different susceptibilities to undergoing ion exchange reactions.

In the present invention, an initial fibrogenic alginate preparation is purified by any suitable means to yield a non-fibrogenic alginate suitable for coating cells. In alternative, a commercially available alginate which is already purified can be used as long as it is substantially non-fibrinogenic. Suitable initial alginate preparations are preferably obtained by isolating alginates from brown algae and are readily commercially available.

One way to purify the alginates is to contact the initial alginate preparations with a divalent metal-ion chelating agent to remove divalent metal ions, and then contact the alginate with high surface area, bleached, activated carbon. The carbon adsorbs polyphenols together with associated protein and fucose moieties. After treatment with carbon, the alginate is precipitated from solution, washed and then filtered to remove additional impurities and to provide the non-fibrogenic alginate of the present invention. However, any other suitable purification method may be advantageously utilized.

Typically, to prepare the non-fibrogenic alginate of the invention, an initial alginate preparation is dissolved in water or buffer, preferably containing a divalent metal-ion chelating compound such as ethylenediamine tetraacetic acid (EDTA), EGTA or sodium citrate, among others, and then contacted with a high surface area, activated carbon to remove any polyphenols and other organic associated contaminants present by adsorption. About fifty grams of alginate is usually dissolved in about 1 to 10, and more preferably about 3 to 8 liters, of water. Suitable activated carbon includes any high surface area activated carbon having a particle size of about 100 mesh or finer. Preferably, very fine activated carbon powder having a surface area of at least about 1,000, and preferably at least about 1,500 $m^2/g$, may be used. Suitable activated carbon is commercially available.

The activated carbon is preferably bleached to oxidize and remove organic contaminants prior to use. The activated carbon may be bleached using a known bleaching agent such as sodium hypochlorite, and the like. The carbon may be bleached by stirring it with a dilute solution of the bleach for a time sufficient to remove any contaminants from the surface of the carbon. This is accomplished by stirring the activated carbon with an about 0.005 to 0.50M, and more preferably an about 0.08 to 0.10M, sodium hypochlorite solution for about 5 to 30 minutes, and preferably about 10 to 20 minutes, which is sufficient to oxidize the activated carbon. After oxidation, the activated carbon may be removed from the dilute bleach solution by centrifugation or filtration, washed with ethanol and water, and dried. The ratio (w/w) of initial alginate to activated carbon is usually about 1:1 to 1:20, and more preferably about 1:2 to 1:8. The amount of activated carbon may be adjusted as necessary to insure the removal of contaminants sufficient to achieve the minimum amounts permitted by this invention.

The alginate solution and bleached carbon are contacted by simple mixing, shaking or rolling, and the bleached carbon is then removed by conventional centrifugation and filtration. Preferably, the filtration is conducted using sequentially finer sub-micron filters.

A monovalent cation salt solution is then added to the filtered alginate solution in an amount sufficient to allow precipitation of the alginate by addition of ethanol. Any soluble monovalent cation salt may be used. Sodium chloride solution of about 0.05 to 1.0M is preferred.

The alginate is then precipitated from the resulting solution by addition of ethanol with stirring. Generally, the ratio (v/v) of ethanol to alginate solution is about 0.25 to 2.0, and preferably about 0.5 to 1.5. The precipitated alginate is then recovered by filtration, washed with ethanol and dried to remove any traces of ethanol.

The alginate obtained as described above is directly suitable for coating a transplant tissue or cells without the use of additional coating compounds such as homopoly(amino acids), e.g., polylysine. However, it is possible, if desirable, to further purify the alginate or chemically modify the properties of the alginate to tailor the alginate coating to provide specific properties. Important properties of the alginate coating materials include, for example, a well defined and controlled pore size providing a desirable permeability of the coating for diffusion of materials to and from the encapsulated core; the coating thickness of each layer; the viscosity of coating solutions and the mechanical strength of the coating.

The average molecular weight and overall mannuronate to guluronate molar ratios are initially substantially determined by the origin of the material, but may be further adjusted by physical and chemical methods. Typically, the molecular weight of suitable alginate is within the range from 20–500 kilodaltons. The molecular weights may be reduced, for example, by partial acid hydrolysis, thermal degradation or sonication. High molecular weights may be obtained by controlled precipitation methods with concomitant alteration of uronic acid composition, or by dialysis, molecular filtration, or gel exclusion chromatography. The mannuronate to guluronate ratio and sequence distribution is typically increased or decreased by selective precipitation or solubilization by monovalent or divalent metal cations, organic solvents or acids. Adjustment of these characteristics provide optimum alginate properties for coating of different tissue transplants.

The appropriate concentration of an alginate in solution is a function of the physical properties of the alginate. At very low concentrations the coating morphology is poor, resulting in ineffective coatings. At very high concentrations, the viscosity is too high to form coatings of appropriate thickness. Preferably, the relative amount of mannuronate and guluronate in the alginate is to from 1:6 to 6:1 and can be adjusted by, for example, dissolving precipitated alginate in a solution, for example about 0.05 to 1.00M potassium chloride, to redissolve guluronate-rich fractions while mannuronate-rich fractions are left in the precipitate. The insoluble material may be collected by centrifugation. The redissolved guluronate-rich material is then reprecipitated by addition of ethanol. By repeating this process, different relative proportion of mannuronate and guluronate in the alginate is obtained.

Homopolymeric polymannuronate and polyguluronate alginate sequences are generally acid-insoluble, whereas alternating mannuronate-guluronate sequences are for the most part acid-soluble. By extracting the alginate with an acid solution of pH about 1.5 to 2.5, and preferably having pH about 2.0, it is possible to selectively solubilize alternating mannuronate-guluronate block-rich alginates. Additionally, mannuronate-rich alginates are preferentially solubilized relative to guluronate-rich alginates. The treatment of an alginate with an acidic solution, therefore, precipitates guluronate-rich alginates preferentially leaving mannuronate-rich and particularly alternating mannuronate-guluronate-sequence-rich alginates in solution. The separation of the precipitate from the solution thus provides both guluronate-rich and heterogeneous block and mannuronate-rich alginate fractions. The guluronate-rich alginate present in the solution is precipitated by the addition of calcium ions or ethanol. Alternatively, the guluronate-rich alginate can be obtained by precipitation of the guluronate-rich fractions with calcium ions while leaving the mannuronate-rich fractions in solution. After separation of the precipitate from the solution, the mannuronate-rich alginate fraction is precipitated from solution by addition of acid or ethanol. The proportions of acid and/or calcium precipitated materials is controlled by adjusting the pH and the calcium concentration, respectively.

It is also possible to obtain specific relative amounts of mannuronate and guluronate in the alginate coating by mixing different mannuronate-rich fractions and guluronate-rich fractions obtained as described above. By sequentially adding small portions of guluronate-rich material to mannuronate-rich material, the amount of guluronate in the overall alginate composition may be gradually increased, thereby increasing the number of divalent metal ion binding sites in the overall coating, increasing the structural rigidity of the coating, and producing larger pore sizes. For any particular mixture of mannuronate-rich and guluronate-rich fractions, the relative amount of mannuronate or guluronate in the alginate may be readily determined by NMR spectroscopy. The average molecular weight and porosity of the alginate coating can be adjusted by mixing mannuronate-rich and guluronate-rich fractions in different proportions.

The mannuronate to guluronate molar ratio of the coating polymer is typically from 1:6 to 6:1.

The current alginate coating is substantially free from fucose, polyphenol, protein and other impurities. The amount of fucose groups in the coating is, in general, less than about 0.2 micrograms per milligram of sodium alginate (even less than about 0.02 wt. %) and the amount of polyphenol groups is, in general, less than about 2.0 micrograms of tannin-equivalents per milligram of sodium alginate (even less than about 0.2 wt. %).

All alginates described above and any and all their mixtures and combinations or any other suitable alginates are intended to be within the scope of this invention as long as these mixtures will result in a coating having the properties intended by the current method.

III. MECHANISM OF ALGINATE GELLING AND HALO LAYER PRODUCTION

The basic premise of the present invention is to first produce initial transplant coating which comprise a stable gel coating of alginate interacted with any of the divalent crosslinking ions. Most divalent cations can be successfully utilized, however calcium, strontium or barium are most suitable and these cations are preferred. Next, these divalent cations may be exchanged for different divalent cations. After removal of soluble cations by washing with a non-ionic medium, the capsules thus prepared can be suspended in a soluble salt of a typically lower molecular weight alginic acid typically having a lower overall ratio of guluronate to mixed or mannuronate blocks, and thus typically having a lower affinity for the divalent cation. Ion exchange, presumably primarily between the non-gelling counterion of the suspending alginate and the gelling divalent cation, results in migration of the divalent cation outward from the surface of the primary coat. As the divalent cation encounters guluronate blocks of the suspending alginate, it engages in interaction with the guluronate which ultimately leads to cooperative stabilization of crosslinked alginate extending beyond the surface of the initial coating. The thickness and stability of this halo layer are dependent upon selection of properties of first and second alginates, alginate concentrations, choice of monovalent and divalent cations and other factors. Exchanging other divalent ions, such as strontium for calcium after initial coating formation, gives rise to a more well-defined, reasonably stable halo layer. Exchanging barium for calcium results in a very stable and well-defined halo and primary coating. When calcium or strontium are used, the time between suspension of coated cells in the second alginate and dispersal of this suspension into droplets to be permanently stabilized by gelation in collecting calcium solution is thus important and is typically between about 15 second to about 5 minutes. Selection of alginates used for first and second coating will influence the nature of the halo and thus the thickness and properties of the final multiple coating.

Since alginates from a variety of different seaweeds having a variety of different chemical and physical properties are readily available commercially, it is possible to select sources for alginates which will be most appropriate for preparing multiple coatings with a desired set of properties. In addition, a number of methods, some listed above, exist for modification of the properties of alginate to provide an additional level of flexibility in controlling the properties of the final multiple coating. For example, acid hydrolysis can be used to decrease average molecular weight and selective salt or acid precipitation can be used to vary mannuronate to guluronate ratio or mixed block to homogeneous block ratio.

Specific examples of alginate preparation and of conditions for forming initial coatings, halos and outer coatings are included in examples.

IV. DROPLET GENERATING DEVICES

Any appropriate type of droplet generating device can be successfully utilized in the process of this invention. Example of such a droplet generating device are the air knife, electrostatic droplet generator and a spinning disc droplet generator. An air knife device is described in copending patent application Ser. No. 08/185,709 filed concurrently on Jan. 24, 1994, now allowed, which is hereby incorporated by reference. An electrostatic droplet generator is subject of the patent application Ser. No. 07/890,982 filed on May 29, 1992, now abandoned, which is hereby incorporated by reference.

A spinning disc droplet generator comprises a rotating bead forming cup means for forming beads and projecting them outward, and a collection basin surrounding the bead forming cup means and axially concentric therewith. The collection basin is mounted for rotation about its central axis and positioned to collect beads projected outward from the bead forming cup means. Elevation adjustment means is connected to coating apparatus for adjusting the alignment of the bead forming cup means with respect to the collection basin in the axial direction. The collection basin is connected to a first rotational drive means. The first rotational drive means includes speed adjustment means for adjusting the rotational speed of the collection basin. The bead forming cup means is preferably attached to a second rotational drive means, and the second rotational drive means includes second means for adjusting the rotational speed of the bead forming cup means. The elevation adjustment means can be a means for elevation of the second rotational drive means. The bead forming cup means has typically an axially concentric mixing chamber, the walls thereof forming an angle of less than 5° with the central axis of the bead forming cup means in a plane through the central axis thereof. The mixing chamber has an upper boundary from which a contiguous bead forming surface extends outward, the bead forming surface forming an angle with the central axis which is sufficient to establish surface contract with the droplets. The bead forming surface can form an angle with the axis thereof of from about 0° up to less than 90° and preferably from 10° to 85° with the central axis of the mixing chamber in a plane through the central axis thereof. The surface of the bead forming surface can be smooth or textured and can have a coating which interacts with the beads to increase the surface-liquid interaction. For example, the surface can be roughened with fine abrasive (such as a fine sandpaper or steel wool) wiped across the surface in a radial direction or an angle thereto, or the surface can have radial grooves. The collection basin comprises a first annular channel having upper and lower rims extending inwardly toward its central axis, the lower rim thereof defining a second annular channel having an upwardly extending inner rim. The second annular channel comprises downwardly converging inner and outer surfaces. The second annular channel includes an annular trough having inner and outer boundaries, the inner surface extending upward from the inner boundary and contiguous therewith, and the outer surface extending upward from the outer boundary and contiguous therewith. The first annular channel has a substantially cylindrical bottom surface and said second rim extends to the bottom surface and is contiguous therewith. The collection basin can comprise a plurality of adjacent annular channels, each channel having upper and lower rims extending inwardly toward its central axis, each lower rim thereof defining a second annular channel having an upwardly extending inner rim. Preferably, the diameter of adjacent channels are not the same.

Any of the above-mentioned and other suitable droplet generating devices can be advantageously utilized.

V. DETAILED DESCRIPTION OF FIGURES

FIGS. 1–7 illustrate the current invention and its utility.

FIG. 1 is a scheme of a process used for production of multiple alginate coatings. The process comprises eight steps. The first step concerns suspending the isolated biological tissue or cells in a soluble first alginate. This alginate contains typically only a relatively small amount of mannuronate and mixed blocks of alternating mannuronate and guluronate. However, a second alginate, described below, or any other suitable alginate may also be advantageously used.

In the second step, the suspension of tissue or cells in soluble alginate is submitted to a droplet generating process, using any suitable droplet generating device, such as an electrostatic droplet generator, air knife or spinning disc droplet generator. In the third step, generated droplets are collected in calcium or other divalent cation solution, thereby causing the alginate to gel to form a distinct first coating. During this process, calcium or other divalent ions interact with the alginate to form a gel. The fourth step comprises exchange of calcium or other divalent cations by barium or strontium or other divalent cations by suspension of the coated cell or tissue in step 3 in a strontium or barium or other divalent cation solution. The second divalent cation (e.g., strontium or barium) is exchanged for the first divalent cation. In alternative, step 4 can be omitted and concentration of the gelling cation can be reduced by washing with a sucrose solution or other non-ionic, iso-osmolar solution. In step 5, excess of soluble divalent cations is washed out with iso-osmolar sucrose solution or with other non-ionic iso-osmolar solution. This solution removes all soluble competing ions except in the case where step 4 is omitted and a reduced concentration of divalent cations is retained within suspended capsules. In the absence of competing soluble ions, barium or strontium or other divalent cations remain bound to alginate and in the case where step 4 is omitted, soluble divalent cation remains within the capsules.

Step 6 is the formation of an intermediate or halo layer by suspending coated cells or tissue recovered from step 5 in a second alginate. The halo layer is formed by the exchange of sodium or other non-gelling cation from the soluble alginate for barium, strontium or other divalent cation bound to the first alginate and/or by diffusion of soluble calcium or other divalent cation from the capsules. The second alginate is gelled by interaction with barium, strontium, calcium or other divalent cation as these ions diffuse outward from the capsules. In the step 7, a final and outer alginate layer is formed by dispersing these capsules from step 6 using an air knife or other droplet generating device. Mechanically generated droplets are collected in a divalent cation solution which causes an outer film of the second alginate to gel and thereby to form an outer alginate gel coating.

FIG. 2 is a drawing showing multiple coated pancreatic islets (A) according to the method of the current invention. Pancreatic islet (A) and several individual pancreatic cells (B) form the core. The core is enclosed in a first initial gelled alginate coating (C) surrounded by a halo layer (D) formed by the exchange of sodium ions by strontium. The outer coating (E) is formed by dispersing halo covered islets and collecting them in calcium solution resulting in the gelling of the outer layer.

Figure 3:
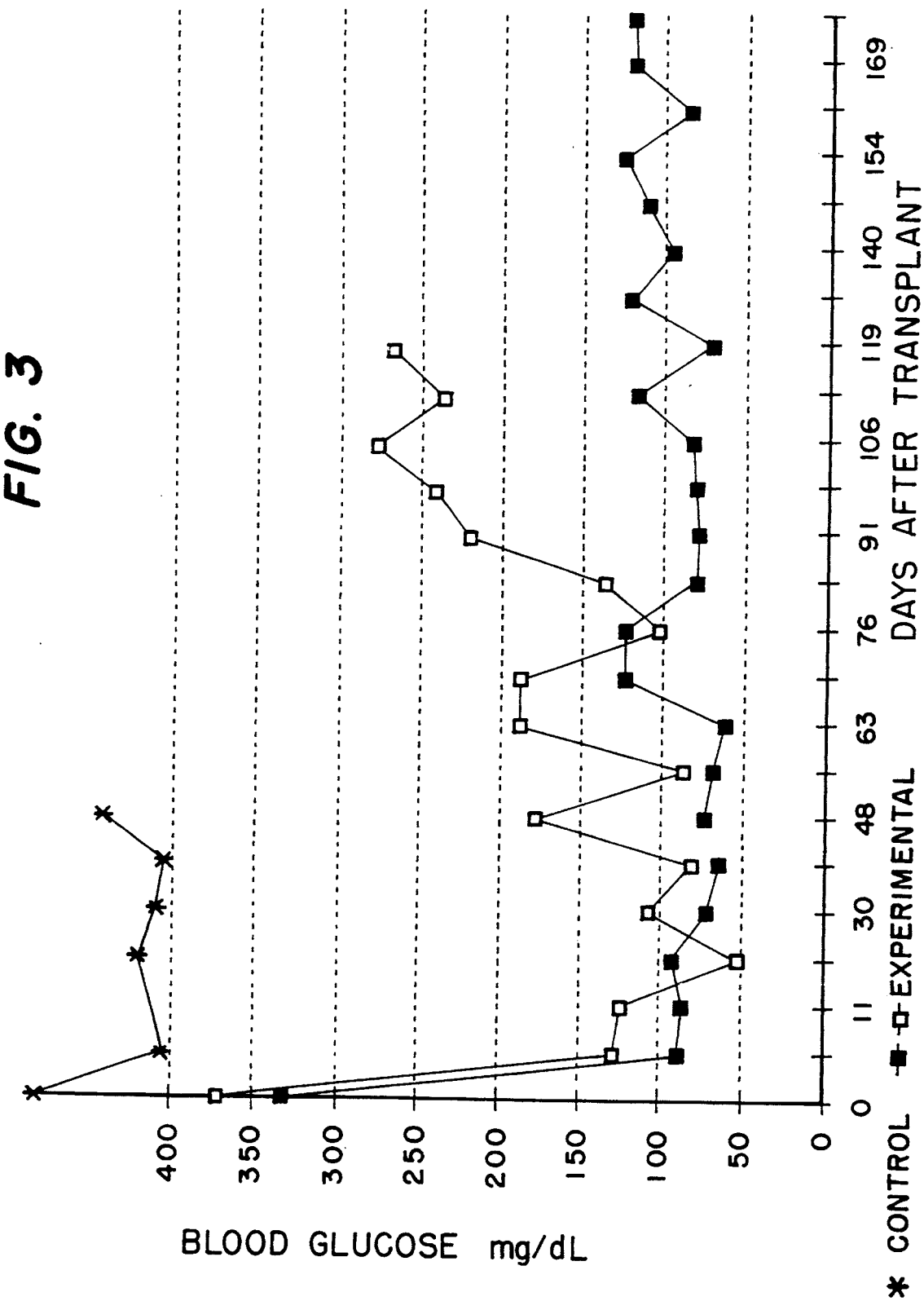
FIG. 3 illustrates blood glucose values observed in streptozotocin induced diabetic mice having been transplanted with multiple alginate layer coated rat islets.

FIG. 3 illustrates the blood glucose levels over 169 days following transplantation of multiple coated islets into immunologically incompatible diabetic mice. Blood glucose values were observed in diabetic BALB/c mice following transplantation of rat islets multiple coated with calcium alginate. The BALB/c mice were rendered diabetic by IP injection of streptozotocin according to Example 8. The rat islets were multiple coated using method as described in Examples 1–5. One to two thousand rat islets coated with multiple layer coatings were injected into the peritoneal cavities of the mice. The mice became euglycemic within the first 5 days following transplantation and remained euglycemic for 80 and 307 days, respectively. Figure shows results only to day 169. Mouse (-□-) died at day 119.

At 307 days, the remaining mouse (-■-) was sacrificed and the coated islets examined. The coated islets were found to be viable and free from fibrosis and macrophage overgrowth. Blood glucose level for this mouse is shown to remain high post transplant for 78 days (FIG. 3).

Empty spheres formed from the same alginate (without pancreatic cells) were injected IP into a control diabetic BALB/c mouse. The mouse was sacrificed at 155 days post-implant. The alginate spheres were examined histologically and found to be free from fibrosis and substantially free from macrophage overgrowth.

Figure 4:
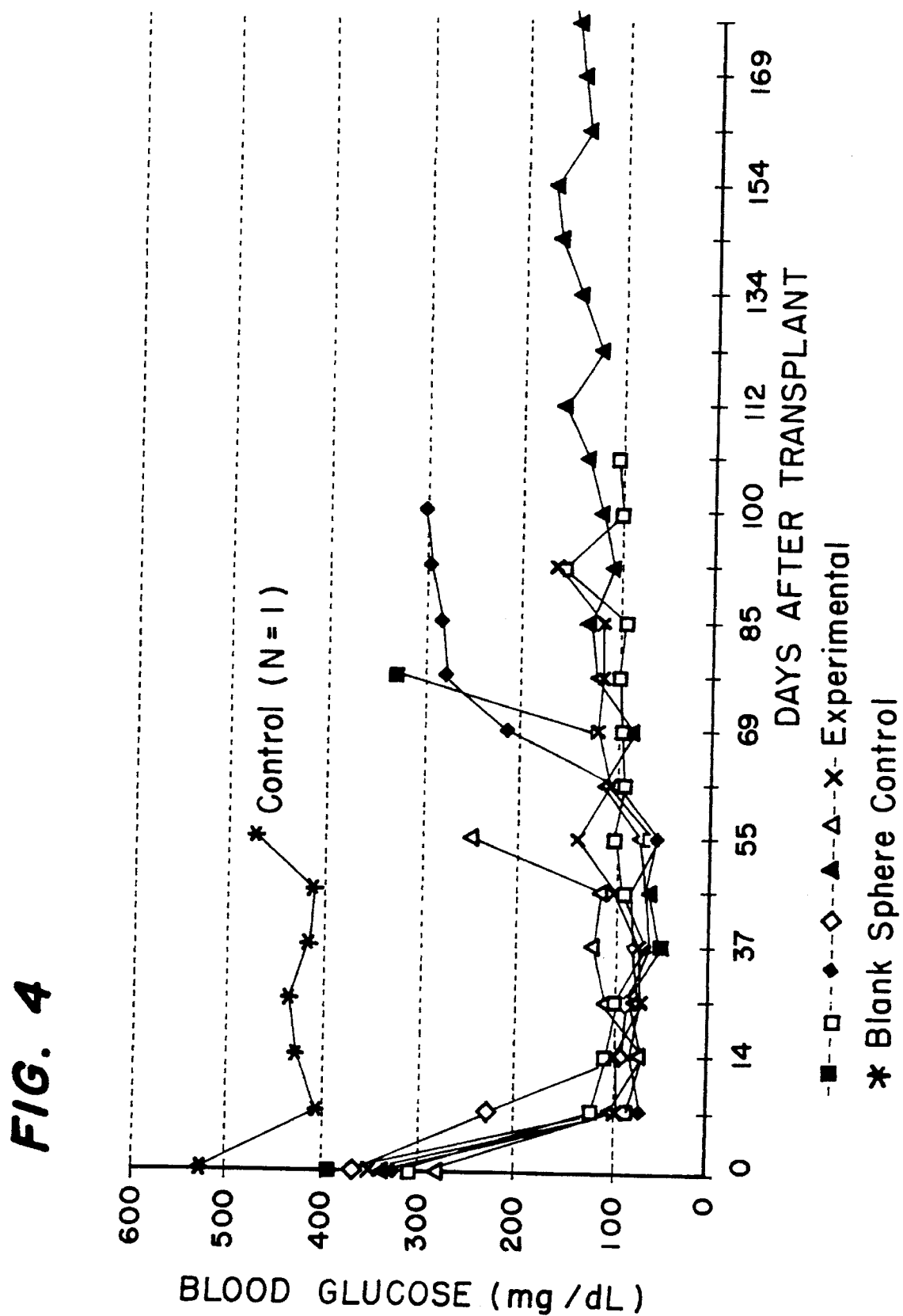
FIG. 4 shows blood glucose values observed in streptozotocin-induced diabetic mice having transplanted multiple alginate coated dog islets.

FIG. 4 illustrates another study of the transplantation of coated islets into immunologically incompatible individuals. Blood glucose values of experimental and control mice (receiving blank capsules) were observed in diabetic BALB/c mice following transplantation of multiple alginate coated dog islets. The dog islets were coated using the method as described in Examples 1–5. The BALB/c mice were rendered diabetic by IP injection of streptozotocin as in Example 8. One to two thousand coated dog islets were transplanted into the peritoneal cavities of the mice. The mice became euglycemic within 7 days following transplantation and remained euglycemic for 40 to 183 days.

From seven mice used in this experiment, one mouse (-▲-) remained euglycemic for 183 days when it was sacrificed. A second mouse (-□-) remained euglycemic until day 106 when it died. A third mouse (-X-) remained euglycemic until day 90 when it died. A fourth mouse (-■-) remained euglycemic until day 69 and was sacrificed at day 78. The fifth mouse (-Δ-) was euglycemic until day 54 and was sacrificed on day 55. The sixth mouse (-◇-) was euglycemic for 56 days when it was sacrificed. The seventh mouse (-♦-) was euglycemic until day 69. Then the blood glucose went up and the mouse was sacrificed on day 134. Of the group, five animals remained euglycemic for at least 70 days, with three of them longer. The longest surviving mouse remained euglycemic until sacrificed at day 183. Two other animals were euglycemic for at least 50 days following the transplantation of pancreatic islets coated according to this invention. Control mouse remained hyperglycemic until day 55 when it died.

All of the mice were sacrificed or died and the coated islets were examined. Viable alginate-coated islets found in all mice were free from fibrosis and free from macrophage overgrowth. The reason some animals returned to a diabetic state may have been an insufficient number of viable, coated islets administered.

Figure 5:
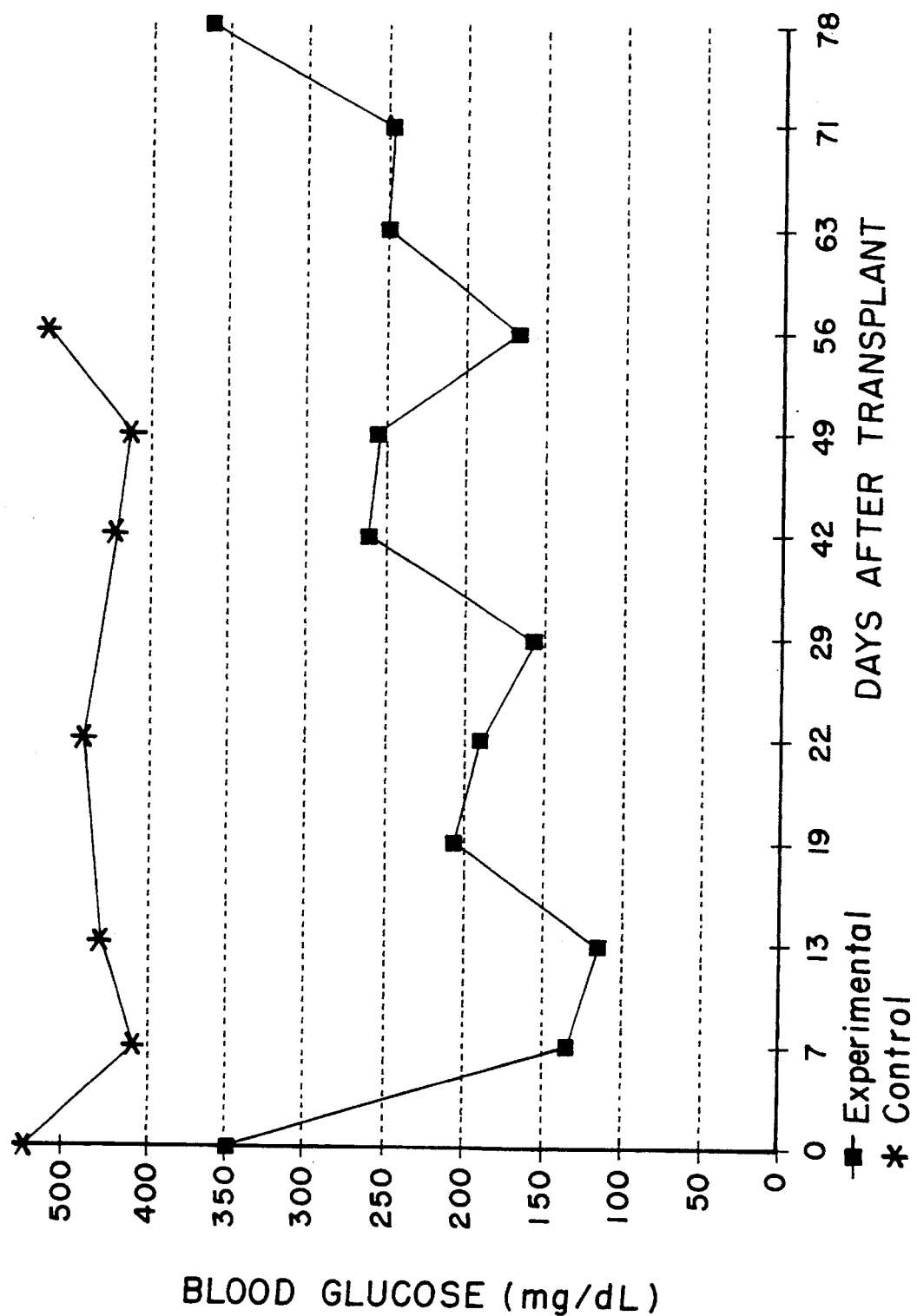
FIG. 5 shows blood glucose values observed in streptozotocin-induced diabetic mice having transplanted multiple alginate coated dog islets.

FIG. 5 illustrates blood glucose values observed in diabetic BALB/c mice following transplantation of multiple alginate coated dog islets crosslinked alginate with strontium (N=1) or blank capsules (N=1). The dog islets were single coated using high guluronate alginate as described in Examples 1, 4, 5, and 7. Then, multiple coatings were applied to the single coated islets as described in Example 2, 4, and 7. The BALB/c mice were rendered diabetic by IP injection of streptozotocin. One thousand coated islets were transplanted into the peritoneal cavity of the experimental mouse (Example 8). Equivalent number of blank capsules were transplanted into the control mouse. Blood glucose levels of the experimental mouse decreased following transplantation and remained lower for 71 days.

The mouse was sacrificed at day 78 and the coated islets examined. The coated islets were found to be viable, free from fibrosis and free from macrophage overgrowth.

The control mouse was sacrificed at 56 days post-transplant. The alginate spheres were examined histologically and found to be free from fibrosis and substantially free from macrophage overgrowth.

FIG. 6 illustrates results obtained with transplantation of dog pancreatic islets to an experimental diabetic dog. The islets were single coated with alginate.

The dog was made diabetic by total pancreatectomy. Following surgery, her blood glucose level was 325 mg/dL and she required 6–7 units of insulin to maintain her blood glucose level below 150 mg/dL.

Four hundred thousand islets were isolated from unrelated dog pancreases. The islets were coated with a single alginate coating as described in Example 4. The single alginate coated islets were transplanted into the peritoneal cavity of the diabetic dog using an 18 g needle. After each transplantation (days 0, 7, 20 and 28) her blood glucose level and insulin requirement declined only to return to the pre-transplant level suggesting death of the single coated islets. On day 35 (7 days after the last transplant), the animal returned to the diabetic state, requiring 5–6 units of insulin to maintain blood glucose below 150 mg/dL. The dog was sacrificed and the coated islets were examined and found to be fibrosed where islets were exposed.

Figure 7:
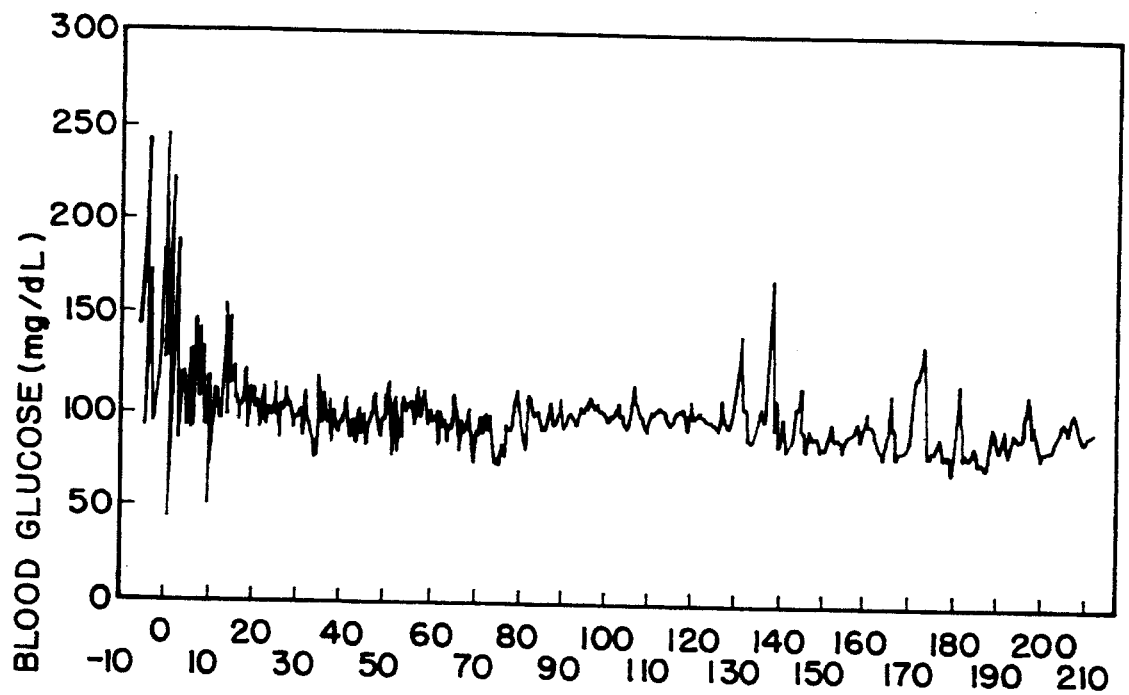
FIG. 7 depicts survival, blood glucose levels, and levels of administered insulin in a pancreatectomized dog transplanted with multiple alginate coated dog islets, for 210 days after transplantation.
Figure 7A:
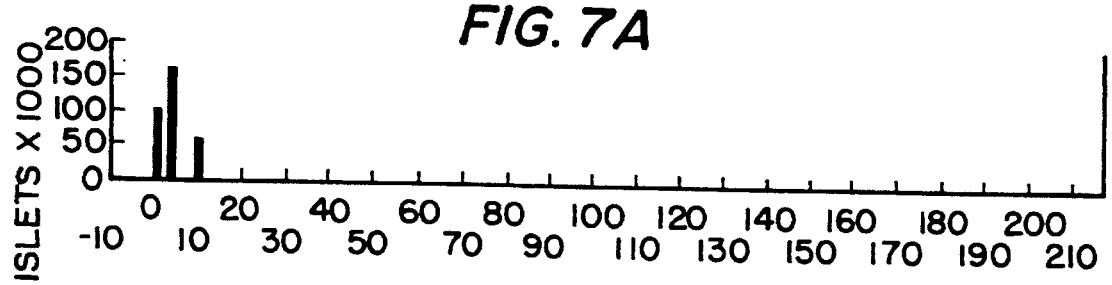
Figure 7B:
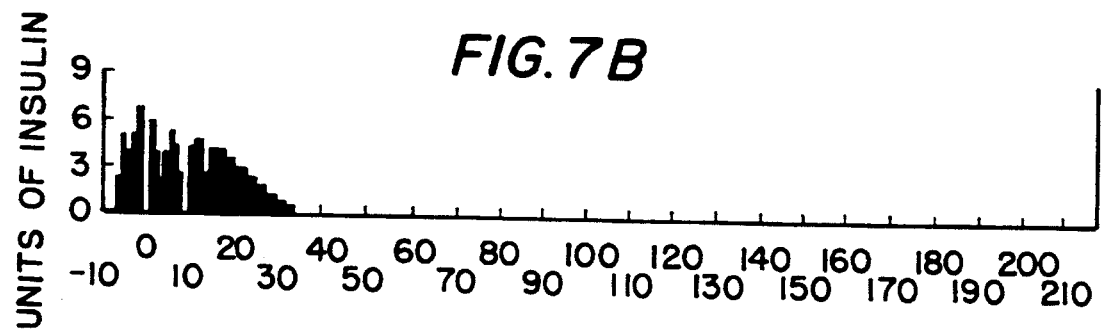

FIG. 7 illustrates the results obtained with transplantation of unrelated dog pancreatic islets coated with multiple layer coatings according to the invention.

The dog was made diabetic by total pancreatectomy. Following surgery her initial blood glucose level was 250 mg/dL and she required 5–7 U of NPH insulin to maintain it below 150 mg/dL.

Three hundred thousand islets were isolated from unrelated dog pancreases. The islets were coated with multiple alginate coating using the method as described in Examples 1–5.

The multiple alginate coated islets were transplanted into the peritoneal cavity of the diabetic dog with a 14 g gauge needle. After each transplantation (day 0, 3 and 10) her blood glucose level and insulin requirement declined within hours. The transplanted multiple alginate coated islets have continued to function for over 200 days and the dog is still alive and remains euglycemic. The dog has had intermittent elevation (days 128 and 139) in her blood glucose levels from about 140–175 mg/dL. This may indicate that more islet mass may be needed to maintain blood glucose levels below 120 mg/dL.

Additionally, the multi-layer coating was tested on other types of cells and tissues. Calcitonin producing cells were coated according to the invention and their viability tested by using trypan blue/dye exclusion and alamar Blue assays. These assays demonstrated that there were viable cells and continued cell growth in the population. In vitro experiments were used to follow containment, growth and product secretion. The procedures are described in Examples 10 and 11.

Similarly, hepatocytes were coated according to the invention and their viability and functionality was tested, as described in Example 11.

UTILITY

The transplants coated with multiple layer coating according to the current invention are useful for treatment and correction of dysfunctions, deficiencies, and disturbances such as diabetes mellitus, hypothyroidea, hypoparathyroidea, Cushings disease, hemophilia and others.

The method can be used to coat any biologically active tissues or cells. All living tissues or cells which produce biologically active substances intended to be implanted into the body of a host animal can be coated and implanted as coated transplants by using this method. These tissues and cells include without limitation, tissue, cells and cell lines removed from a donor human or animal, tissue and cells, and cell lines obtained by incubation or cultivation of donor tissues and cells, cells obtained from viable cell lines, biologically active products of cells and tissues, and the like. Any type of tissue, cell or cell line for which transplantation is desired can be coated and transplanted according to this invention.

Important tissues for transplants are secretory organ tissues, where transplantation from a donor organ to a host animal is desired to at least partially replicate the donor organ's function in the host system. Preferred donor tissues are pancreatic islets, hepatic cells, neural cells, renal cortex cells, vascular endothelial cells, thyroid cells, adrenal cells, thymic cells and ovarian cells. However, other types of cells may also be utilized. The invention is particularly advantageous for coating pancreatic islets, hepatic cells, and other endocrine tissues and cells.

Coating agents must be physiologically acceptable and non-toxic to the biologically active material being coated and to the host tissue. The coating must be non-fibrogenic. Coatings having an outer negative charge such as alginates are typically most suitable. The most preferred alginates are free from fibrogenic concentrations of fucose, sulfate, phloroglucinol and protein moieties and other impurities.

The multiple coating according to the current invention assures the immuno-resistance of the biological material such as coated cells or tissue, while at the same time preserving the functionality of the coated cells or tissue and diffusion of the secreted hormone or product of the cells or tissue and exchange of nutrients and secretion and waste products in and out of the formed coated capsules containing a core of biological tissue or cell.

Implantation is typically by simple injection through a hypodermic needle having a bore diameter sufficient to permit passage of a suspension of coated cells therethrough without damaging the tissue coating. For implantation, the coated transplant tissues are formulated as pharmaceutical compositions together with a pharmaceutically acceptable carrier. Such compositions should contain a sufficient number of coated transplant capsules which can be injected into an animal.

Typically, the number of transplanted islets is within 10 to 30 thousand per kg of body weight. In animal studies, mice were transplanted with 3 thousand coated islets, the dogs were transplanted with about 200–400 thousand coated islets. For human transplantation several million of pancreatic islets may be needed. The number for other cells, tissues or cell lines will be calculated depending on their function.

This invention is further illustrated by the following specific but non-limiting examples.

EXAMPLE 1

Preparation of High Guluronate Alginate

This example illustrates preparation of alginates having high content of guluronate used as a first coating.

Eighty grams of protein alginate commercially available from Protan Biopolymers, Trondheim, Norway, were dissolved in 89 L water by rolling on a roller mill. The solution was filtered through a 50 micron mesh to remove particles, and then mixed on a roller mill with 320 g of bleached, activated charcoal with continued mixing for 30 minutes. The activated charcoal was then removed by centrifugation for 30 minutes. The resulting solution was sequentially filtered through filter paper, a 0.45 micron filter, a 0.22 micron filter and a 0.1 micron filter. 163 g magnesium chloride were then added to the solution and dissolved by rolling on a roller mill. 210 ml of a 1.7% calcium chloride dihydrate solution were then added and mixed by rolling on a roller mill for 30 minutes. The resulting solution was centrifuged for 30 minutes to produce an alginate pellet. The alginate pellet was dissolved in 3.0 liters of 0.1M EDTA, pH 7.0 by rolling on a roller mill. The pH of the solution was adjusted to pH 7.0, as needed. 20 g sodium chloride were then added to this solution and dissolved.

Alginate was precipitated from the solution by the addition of 5 L of neat ethanol, followed by centrifugation for 30 minutes to obtain an alginate pellet. The alginate pellet was then suspended in ethanol and tweezed apart with tweezers to insure complete washing of the sample. Excess ethanol was then removed by squeezing and pressing the precipitate. The alginate precipitate was then dried in an oven, under vacuum, at 60° C.

EXAMPLE 2

Preparation of High Mannuronate Alginate

This example illustrates preparation of alginates having high content of mannuronate.

50 g low viscosity sodium alginate (LV Alginate, KELCO Div. of Merck & Co., San Diego, Calif.) isolated from Macrocystis pyrifera were dissolved in 5 liters of water and filtered through a 50 micron mesh to remove particulates. 18.6 g tetrasodium EDTA were added to the solution and dissolved. The solution was mixed on a roller mill with 200 g hypochlorite-bleached activated charcoal (Mallinckrodt activated charcoal powder) for 30 minutes to remove organic contaminants such as polyphenols. Activated charcoal was then removed by centrifugation for 30 minutes. The resulting solution was sequentially filtered through filter paper, a 0.45 micron filter, a 0.22 micron filter and a 0.1 micron filter. 30 g sodium chloride were then added to the addition of 5 L neat ethanol. The sample was centrifuged for 30 minutes to obtain an alginate pellet and the alginate pellet was suspended in ethanol and then teased apart with tweezers to insure complete washing of the sample. Excess ethanol was removed by squeezing and pressing the precipitate. The resulting precipitate was dried in an oven, under vacuum, at 60° C.

EXAMPLE 3

Preparation of Pancreatic Islet Suspension

This example illustrates the preparation of islets in an alginate suspension.

Pancreatic islets were isolated from dog by collagenase digestion using the method of Warnock GL, Kneteman NM, Evans MG, et al., *Can. J. Surg.*, 33:368, (1990). The final suspension of 37,000 isolated islets in 50 ml tissue culture medium (GIBCO CMRL-1066 with 25 mM HEPES, 10% Hy Clone FBS, 2 mM L-glutamine, 100 μg penicillin/ml, 100 μg streptomycin/ml) was gravity sedimented at room temperature for 15 minutes. The medium was diluted with isotonic saline by removing 25 ml medium and replacing it with 25 ml saline. The 15 minute gravity sedimentation was repeated. The supernatant was removed to 5 ml. The islets were transferred to a 15 ml conical centrifuge tube (Corning 430055) and diluted 1:3 by the addition of 10 ml saline. After a 10 minute gravity sedimentation, the supernatant was removed and the islets resuspended in 15 ml saline. The supernatant was removed to a final volume of 0.2 ml islets in saline. 0.05 ml of 3.44% sodium citrate dihydrate with 10 mM HEPES and 2.25 ml 1% high guluronate alginate (Example 1) was added to the islet suspension giving a final concentration of 14,000 islets in 0.9% alginate in saline with 10 mM HEPES and 6 mM citrate. The final suspension of islets ranges from 10,000–35,000 islets/ml of 0.7–1.0% alginate.

Pancreatic islets were isolated from 10 rats using the method by Lacy PE, Koztianvosky M. in *Diabetes*, 16:35, (1967). The 5,000 islets in 50 ml CMRL tissue culture medium were gravity sedimented at room temperature and washed with saline as for the dog above. The final supernatant was removed to 0.375 ml of islets in saline. 0.075 ml citrate and 1.05 ml 1% high guluronate alginate was added to the islet suspension giving a final concentration of 3,000 rat islets per ml of 0 7% alginate in saline with 10 mM HEPES and 6 mM citrate.

EXAMPLE 4

Process for Formation of First Coating

This example illustrates the process for formation of the first calcium alginate coating of cell and tissue transplants.

The 14,000 dog islets suspended in 2.5 ml 0.9% high guluronate alginate prepared by the procedure of Example 3 was removed from the 15 ml centrifuge tube to a 3 ml plastic syringe by using a 16 g 2¼ inch i.v. catheter (Jelco 4062) with the needle removed. The catheter was then replaced with a 20 g blunt needle.

Using a DC electrostatic voltage of 8 KV (provided by a van de Graaff generator) between needle tip and grounded 0.117M aqueous calcium chloride solution at ambient temperature, a suspension of pancreatic islets (14 dog islets per μl) prepared by the procedure of Example 2 was passed through a 20 gauge needle at a flow rate of approximately 200 μl/min. The suspension emerged from the needle as a thin, attenuated stream which transformed into droplets, the droplets being collected in a 60 mM petri dish (Flacon 1007) containing 10 ml calcium chloride solution. The droplets were gelled by reaction with the calcium ions in the solution. The calcium alginate coatings on the islets were smooth and uniform and had an approximate thickness of about 130 μm. The total coated particles had an average diameter of about 360 μm.

This process was repeated with a suspension of 14 rat islets/μl prepared by the procedure of Example 3.

EXAMPLE 5

Process for Preparation of Multiple Coated Pancreatic Islets Transplants with Calcium Alginate This example illustrates the process for preparation of multiple coated dog pancreatic islets transplants using an extension of the calcium alginate crosslinking.

The islets were prepared according to Example 3 and coated according to Example 4. The single coated islets in spheres were divided into two samples of 1 ml spheres per 50 ml centrifuge tube (Corning 25339-50) in the calcium chloride collecting solution. The concentration of the calcium chloride was reduced from 120mM to 24 mM by adding 40 ml sucrose water to 10 ml of calcium chloride solution containing the 1 ml spheres. After room temperature gravity sedimentation, all fluid was removed from the spheres. To one ml of spheres, 1.5 ml sucrose water was added quickly followed by 8 ml 4% high mannuronate alginate solution (Example 2) while vortexing. The mixture was rotated in the mixing tube for about 2 minutes. The outer coat was formed by using a spinning disc droplet generator, collecting the spheres in about 100 ml calcium chloride solution.

The spheres were gravity sedimented in three 50 ml centrifuge tubes. Each supernatant was removed to 15 ml so that all three could be combined into one 50 ml tube. After another gravity sedimentation, the supernatant was reduced to 15 ml, including 7.5 ml spheres, and 35 ml saline added for a dilution of 1:3. After sedimentation, the process was repeated, making a 1:10 dilution by adding 40 mls of saline to 10 mls of the solution containing the spheres. The final calcium concentration was 4–6 mM.

EXAMPLE 6

Process for Preparation of Multiple Coated Pancreatic Islet Transplants with Barium Crosslinked Alginate This example illustrates the process for preparation of multiple coated pancreatic islet transplants with barium crosslinked alginate halo.

The islets were prepared according to Example 3 and coated according to Example 4.

Excess calcium was removed from 1 ml spheres containing the islets by gravity sedimentation, removal of the supernatant, and resuspension in 15 ml sucrose water three times. Two ml 100 mM barium chloride with 10 mM HEPES was added to 10 ml sucrose water containing the spheres to reach a final concentration of 14 mM barium chloride. The sample was rotated for 5 minutes at room temperature. Excess barium was removed by washing 3 times with sucrose water as above. The supernatant was reduced to 1 ml and 3 ml 4% high mannuronate alginate (Example 2) was vortexed into the sample. The outer coat was formed by using a spinning disc droplet generator, collecting the spheres in calcium chloride solution. The calcium chloride was diluted to 4–6 mM by washing with saline as in Example 5.

EXAMPLE 7

Process for Preparation of Multiple Coated Pancreatic Islets Transplants with Strontium Crosslinked Alginate This example illustrates the process for preparation of multiple coated pancreatic islet transplants with strontium crosslinked alginate.

The islets were prepared according to Example 3 and primary coated according to Example 4.

Soluble calcium was removed from 0.5 ml spheres containing islets by gravity sedimentation, removal of the supernatant, and resuspension in 15 ml sucrose water, repeated three times. Two ml 120 mM strontium chloride with 10 mM HEPES was added to 8 ml sucrose water containing the spheres to reach a final concentration of 24 mM. The sample was rotated for 15 minutes at room temperature. Excess strontium was removed by washing three times with sucrose waster as above.

All fluid was removed from the 0.5 ml spheres to which was added 1 ml sugar water and 2 ml 4% high mannuronate alginate (Example 2) with gentle mixing. The outer coat was formed by using the air-knife, collecting the spheres in 10 ml calcium chloride solution. The calcium chloride was then diluted to 4–6 mM by washing with saline as in Example 5.

EXAMPLE 8

Transplantation of Pancreatic Islets Coated with Multiple Coating into Diabetic Mice This example illustrates the procedure used for testing the efficacy of the coated pancreatic islets in producing and delivering insulin in diabetic mice.

Host BALB/c mice were rendered diabetic by IP injection of streptozotocin (250 mg streptozocin/kg body weight) in 0.1M citrate buffer, pH 4.5 several days prior to transplant.

Coated islets prepared by the procedure of Example 5 were injected into mice using a 16 g needle and a 3 ml syringe. Each animal received 0.2–2.0 ml spheres containing 500–2000 islets. Nine animals receiving multiple coated dog islets remained euglycemic from 54 days to 180 days. Three animals receiving double coated rat islets remained euglycemic from 63 days to $300^+$ days.

Empty alginate spheres were prepared at the same time and injected i.p. into three diabetic mice. Blood glucose levels remained at 350–500 mg/dL. Mice were sacrificed at intervals and the spheres examined and found to be free from fibrosis or overgrowth by macrophages.

EXAMPLE 9

Transplantation of Pancreatic Islets Coated with Multiple Coating into Diabetic Dog This example illustrates the procedure used for testing the efficacy of the coated pancreatic islets in producing and delivering insulin in diabetic dogs.

A dog was made diabetic by total pancreatectomy. Following surgery her blood glucose level was elevated to 242 mg/dL and she required 5–7 U of NPH insulin to keep it below 250 mg/dL. The animal was transplanted while under a general anesthesia. A 14 gauge angiocatheter was inserted midline into the peritoneal cavity of the dog. After removing the needle, the multiple coated islets were injected through the catheter from a 60 ml syringe. Each syringe contained 10 ml spheres in 50 ml Dulbecco's Medium.

The dog was transplanted with 94,000 multiple coated islets 8 days post pancreatectomy, 154,000 multiple coated islets 3 days later, and 54,000 double coated islets 6 days after that for a total of 300,000 islets. There were an average of 2,300 islets/ml spheres. After transplantation, the dog's blood glucose levels were monitored several times each day. The dog was maintained on an average of 4.5 U insulin/day for two weeks post transplant. The insulin was reduced 0.5 U every two days for the next 20 days and then removed entirely from insulin therapy. The dog has remained euglycemic for 10 months to date.

EXAMPLE 10

Multiple Coating of Calcitonin Secreting Cells

This example illustrates a multiple layer coating of calcitonin secreting cells.

A suspension of a calcitonin secreting cell line, MXH-5, (2.5×10⁶) were coated with alginate according to Examples 1, 2, and 4. The second coating was applied according to Example 6, using barium chloride and an air knife.

After the second coating was applied, coated capsules were tested for viability, and cell functionality by using trypan blue dry exclusion and by alamar Blue assay.

Size of these double coated capsules was determined to be within 50–199 μm (~68%). About 50% of the coated cells were viable and functional. They were able to secrete over 200 pg/ml of calcitonin which was about 50% of the amount secreted by neat uncoated cells in culture.

Other cells maintained in cell culture are coated in a similar manner.

EXAMPLE 11

Multiple Coating of Hepatocytes

This example illustrates coating of isolated hepatocytes.

Hepatocytes are isolated in a manner similar to the isolation of pancreatic cells described in Example 3. Cells are then coated according to procedure described in Examples 4, 5, 6 or 7.

After the second coating is applied, the size of the coated cells is determined and the viability and functionality of the coated cells are tested.

What is claimed is:

1. A method for multiple layer coating of a biological material core with an alginate polymer, said coating having a thickness between about 20 and 200 μm, said method comprising the steps:
   (a) suspending the core in a first solution of a soluble alginate to form a first suspension solution;
   (b) mechanically generating droplets of the suspension;
   (c) gelling the first alginate to form capsules containing the core coated with a first initial coating by collecting the generated droplets of step (b) in a first solution containing a divalent cation;
   (d) reducing concentration of a soluble divalent cation;
   (e) forming an intermediate halo layer by:
      (i) soaking the capsules of step (d) in a solution containing a different divalent cation than that of step (c) and effecting exchange of said different divalent cation with a divalent cation bound to the gelled first alginate layer of step (c); or
      (ii) effecting exchange of the divalent cation present in the first solution of step (c) with a cation present in a second soluble alginate solution; and
      (iii) dispersing the alginate coated capsules in the second alginate solution to form a second suspension solution;
   (f) mechanically generating droplets of the second suspension; and
   (g) gelling the second alginate to form the capsules containing the core coated with the first initial coating layer with the intermediate halo layer and with a second outer coating by collecting the generated droplets of step (f) in the second divalent cation solution.

2. The method of claim 1 wherein the divalent cation in step (e) (ii) is calcium.

3. The method of claim 1 wherein the different divalent cation of step (e) (i) is strontium or barium.

4. The method of claim 1 wherein the multiple layer coating has a substantially uniform thickness of polymer.

5. The method of claim 1 wherein the droplets of step (c) are generated by dispersing the suspension in the air.

6. The method of claim 1 wherein for the formation of the intermediate halo layer in step (e) the capsules are suspended in a third alginate solution to form a third suspension and wherein the droplets of the third suspension are generated mechanically.

7. The method of claim 6 wherein the capsules containing the core are coated with a first alginate coating layer, followed with a third alginate solution coating layer forming the intermediate halo and with a second alginate coating layer.

8. The method of claim 1 wherein a molecular weight of the first alginate is from about 80 to about 300 kilodaltons and wherein an amount of guluronate/mannuronate is higher than the amount of mannuronate/guluronate.

9. The method of claim 1 wherein a molecular weight of the second alginate is from about 40 to about 120 kilodaltons and wherein an amount of mannuronate/guluronate is higher than the amount of guluronate/mannuronate.

10. The method of claim 1 wherein the divalent cations in the solution used in step (c) are selected from the group consisting of barium, calcium and strontium chloride.

11. The method of claim 1 wherein the coated cores are non-fibrogenic.

12. A transplant suitable for transplantation into a host, containing a core of viable, functional and physiologically active biological tissue, cells or a cell line coated with a multiple alginate coating having a thickness between about 20 and 200 μm, said transplant formed by steps:
   (a) suspending the core in a first solution of a soluble alginate to form a first suspension solution;
   (b) mechanically generating droplets of the suspension;
   (c) gelling the first alginate to form capsules containing the core coated with a first initial coating by collecting the generated droplets of step (b) in a first solution containing a divalent cation;
   (d) reducing concentration of a soluble divalent cation;
   (e) forming an intermediate halo layer by:
      (i) soaking the capsules of step (d) in a solution containing a different divalent cation than that of step (c) and effecting exchange of said different divalent cation with a divalent cation bound to the gelled first alginate layer of step (c); or
      (ii) effecting exchange of a divalent cation present in the first solution of step (c) with a cation present in a second soluble alginate solution;
   (f) dispersing the alginate coated capsules in the second alginate solution to form a second suspension solution;
   (g) mechanically generating droplets of the second suspension; and
   (h) gelling the second alginate to form the capsules containing the core coated with the first initial coating layer, with the intermediate halo layer and with a second outer coating by collecting the generated droplets of step (f) in a second divalent cation solution.

13. The transplant of claim 12 wherein the multiple alginate coating conforms to the surface of the core and forms an insoluble immunological barrier.

14. The transplant of claim 12 wherein the first layer is chemically bonded to the core and the intermediate halo layer is chemically bonded to said first layer, and wherein the intermediate layer is covered by the second alginate layer chemically bonded to the intermediate layer.

15. The transplant of claim 12 wherein said core is an allograft.

16. The transplant of claim 12 wherein said core is an xenograft.

17. The transplant of claim 12 wherein the core is a pancreatic islet cell.

18. The transplant of claim 12 wherein said core is an endocrine gland or tissue.

19. The transplant of claim 12 wherein said core is a hepatic cell.

20. The transplant of claim 12 wherein said core is a vascular endothelial cell.

21. A method for applying a multiple alginate coating having a thickness between about 20 and 200 μm on a core of a biological tissue or cells, said method comprising steps:

(a) suspending the core in a first solution of a soluble alginate to form a first suspension solution;

(b) mechanically forming droplets containing the suspended core in the first alginate solution using a droplet generating device;

(c) gelling the first alginate solution with a divalent cation selected from the group consisting of calcium, barium and strontium, to produce gelled capsules;

(d) exchanging the divalent cation of step (c) with another divalent cation selected from the group consisting of calcium, barium and strontium wherein the divalent cation of step (c) is different from the divalent cation of step (d), by dispersing gelled capsules in a solution of divalent cation salt;

(e) removing excess soluble divalent cation by washing the gelled capsules in an iso-osmotic non-ionic solution;

(f) suspending gelled capsules in a second alginate optionally forming an intermediate halo layer;

(g) mechanically dispersing the gelled capsules to remove excess soluble alginate; and (h) gelling the dispersed capsules of step (g) in a divalent cation selected from the group consisting of calcium barium and strontium, to form a second alginate coating.

22. The method of claim 21 wherein the alginate of step (a) has higher content of guluronate than mannuronate and the alginate of step (f) has higher content of mannuronate to guluronate.

23. The method of claim 21 wherein the droplet generating device is an electrostatic droplet generator, air knife or spinning disk.

24. The method of claim 21 wherein the divalent cation of the step (c) is calcium, and the divalent cation of step (d) is strontium or barium.

25. The method of claim 21 wherein the iso-osmotic non-ionic solution is iso-osmotic sucrose.

* * * * *

UNITED STATES PATENT AND TRADEMARK OFFICE
CERTIFICATE OF CORRECTION

PATENT NO. : 5,578,314

DATED : November 26, 1996

INVENTOR(S) : Cochrum, K. et al.

It is certified that error appears in the above-identified patent and that said Letters Patent is hereby corrected as shown below:

Title page, item [73],
Assignee: Add -- Metabolex, Inc., Hayward, California --;

Signed and Sealed this

Sixth Day of May, 1997

*Attest:*

BRUCE LEHMAN

*Attesting Officer*   *Commissioner of Patents and Trademarks*